United States Patent
Maxwell et al.

(10) Patent No.: US 6,883,638 B1
(45) Date of Patent: Apr. 26, 2005

(54) ACCELEROMETER TRANSDUCER USED FOR SEISMIC RECORDING

(75) Inventors: Peter Maxwell, Missouri City, TX (US); Lawrence P. Behn, Houston, TX (US); Eugene D. Bednar, Austin, TX (US); Jeffery C. Gannon, Houston, TX (US); Michael Arthur Corrigan, The Woodlands, TX (US); Glen Ragan, Sugar Land, TX (US); Dale J. Lambert, Mandeville, LA (US); Henry Thomas Polk, Houston, TX (US); Steven L. Roche, Sugar Land, TX (US); Wilfred Roy Bertrand, Meadows Place, TX (US); David Wilson, Missouri City, TX (US); Byron Lee Cain, Houston, TX (US); Michael George McMahon, Stafford, TX (US); John C. Downey Jr., Houston, TX (US); Keith Elder, Richmond, TX (US)

(73) Assignee: Input/Output, Inc., Stafford, TX (US)

( * ) Notice: Subject to any disclaimer, the term of this patent is extended or adjusted under 35 U.S.C. 154(b) by 0 days.

(21) Appl. No.: 09/936,629

(22) PCT Filed: Mar. 16, 2000

(86) PCT No.: PCT/US00/06905

§ 371 (c)(1),
(2), (4) Date: Feb. 7, 2002

(87) PCT Pub. No.: WO00/55646

PCT Pub. Date: Sep. 21, 2000

Related U.S. Application Data

(60) Provisional application No. 60/125,076, filed on Mar. 17, 1999.

(51) Int. Cl.⁷ .................................................. G01V 1/40

(52) U.S. Cl. .................. 181/102; 181/108; 181/112; 181/139; 367/14; 367/32; 367/117; 340/870.05; 73/1.01; 73/1.37; 73/570; 73/579

(58) Field of Search .................. 181/0.5, 101–123, 181/139; 73/1.01, 579–583, 1.37, 570, 1.39, 514.05, 382 G, 514.37; 340/870.05, 10.34, 853.3, 17, 3.1, 853.1–2; 367/14, 25, 32, 117, 16, 191, 19, 20; 702/9

(56) References Cited

U.S. PATENT DOCUMENTS

| | | | | |
|---|---|---|---|---|
| 3,877,313 | A | * 4/1975 | Ferriss | .................... 73/514.05 |
| 4,068,208 | A | * 1/1978 | Rice et al. | .................... 367/19 |
| 4,210,897 | A | 7/1980 | Hutchins | |
| 4,437,175 | A | 3/1984 | Berni | |
| 4,841,772 | A | * 6/1989 | Paik | ........................ 73/382 G |
| 4,912,471 | A | * 3/1990 | Tyburski et al. | ......... 340/10.34 |
| 4,922,756 | A | 5/1990 | Henrion | |
| 4,932,261 | A | 6/1990 | Henrion | |
| 5,060,504 | A | * 10/1991 | White et al. | ............. 73/514.37 |

(Continued)

FOREIGN PATENT DOCUMENTS

| | | | |
|---|---|---|---|
| JP | 08285952 | | 1/1996 |
| WO | WO98/14800 | * | 9/1997 |
| WO | WO98/12577 | | 3/1998 |

*Primary Examiner*—David Martin
*Assistant Examiner*—Renata McCloud
(74) *Attorney, Agent, or Firm*—Madan, Mossman & Sriram, P.C.

(57) ABSTRACT

Method for operating and testing a sensor assembly (210). The sensor assembly (210) preferably includes accelerometers with axes of sensitivity orthogonal to each other. The method preferably includes determining sensor tilt angle, determining the position of the sensor, and synchronizing the operation of the sensor.

3 Claims, 34 Drawing Sheets

U.S. PATENT DOCUMENTS

| | | | | |
|---|---|---|---|---|
| 5,160,925 A | * | 11/1992 | Dailey et al. | 340/853.3 |
| 5,433,101 A | * | 7/1995 | Spangler et al. | 73/1.39 |
| 5,724,241 A | | 3/1998 | Wood et al. | 364/421 |
| 5,842,149 A | * | 11/1998 | Harrell et al. | 702/9 |
| 5,852,242 A | | 12/1998 | Devolk et al. | |
| 6,028,817 A | * | 2/2000 | Ambs | 367/16 |
| 6,075,754 A | * | 6/2000 | VanZandt et al. | 367/182 |
| 6,101,864 A | * | 8/2000 | Abrams et al. | 73/1.01 |
| 6,255,962 B1 | * | 7/2001 | Tanenhaus et al. | 340/870.05 |
| 6,430,105 B1 | | 8/2002 | Stephen | |
| 6,497,149 B1 | | 12/2002 | Moreau et al. | |
| 6,512,980 B1 | * | 1/2003 | Barr | 702/1 |

\* cited by examiner

ACCELEROMETER TRANSDUCER USED FOR SEISMIC RECORDING

This appln. is a 371 of PCT/US00/06905 Mar. 16, 2000 which claims benefit of provisional appln. 60/125,076 Mar. 17, 1999.

BACKGROUND OF THE INVENTION

The present disclosure relates generally to apparatus and methods for operating and testing a sensor assembly, and in particular to a multi-axis accelerometer sensor assembly.

In operating a multi-axis accelerometer sensor assembly, certain parameters are required to analyze the data acquired from the multi-axis accelerometer sensor assembly. The operating parameters that are used for analysis typically include tilt angle, sensor orientation, ground-coupling, position of the sensor assembly, and synchronization of the operation of the sensor assembly. The state-of-health of the sensor assembly is also typically required to validate the operation of the sensor assembly.

The present invention is directed at acquiring the necessary parameters for data analysis and validating the operation of the sensor assembly.

SUMMARY OF THE INVENTION

According to one aspect of the present invention, a system for acquiring seismic data is provided that includes one or more sensor modules adapted to sense seismic data and one or more seismic recorders adapted to record seismic data and coupled to the sensor module.

According to another aspect of the present invention, an apparatus for sensing seismic energy is provided that includes a sensor adapted to sense seismic energy, and the sensor includes one or more accelerometers, and the accelerometers include one or more axes of sensitivity.

According to another aspect of the present invention, an apparatus for sensing seismic energy is provided that includes a sensor adapted to sense seismic energy, and the sensor includes one or more micro-machined sensor elements.

According to another aspect of the present invention, an apparatus for synchronizing the operation of a sensor to a common time base is provided that includes a sensor module adapted to sensing seismic energy, and the sensor module includes one or more sensors, and the sensor module further includes a global positioning system receiver adapted to synchronize the operation of the sensors.

According to another aspect of the present invention, an apparatus for synchronizing the operation of a sensor to a common time base is provided that includes one or more accelerometers adapted to sensing seismic energy; and a seismic recorder coupled to the accelerometers, and the seismic recorder includes a global positioning system receiver adapted to synchronize the sensor.

According to another aspect of the present invention, an apparatus for determining the position of a sensor is provided that includes a sensor module adapted to sense seismic energy, and the sensor module includes a global positioning system receiver adapted to determine the location of the sensor module.

According to another aspect of the present invention, an apparatus with insensitivity to tilt for sensing seismic energy is provided that includes a sensor adapted to sense seismic energy; a feedback control circuit adapted to provide force balanced feedback coupled to the sensor; and a controller adapted to monitor the operation of the apparatus coupled to the sensor.

According to another aspect of the present invention, an apparatus for determining the orientation of a sensor is provided that includes a sensor module adapted to sense seismic energy; and a controller adapted to control the operation of the apparatus coupled to the sensor module, and the sensor module includes a 3-axis magnetometer adapted to determine the orientation of the sensor module.

According to another aspect of the present invention, an apparatus for determining the coupling between a sensor and the ground is provided that includes a sensor adapted to sense seismic energy; a crystal assembly adapted to provide a force in order to measure the ground coupling of the sensor coupled to the sensor; and a controller adapted to control the operation of the apparatus coupled to the sensor.

According to another aspect of the present invention, an apparatus for measuring the vector fidelity of a sensor is provided that includes a sensor adapted to sense seismic energy; a crystal assembly adapted to provide a force in order to measure the vector fidelity of the sensor coupled to the sensor; and a controller adapted to control the operation of the apparatus coupled to the sensor.

According to another aspect of the present invention, a method of seismic sensing is provided that includes monitoring acceleration in a plurality of directions.

According to another aspect of the present invention, a method of seismic sensing is provided that includes monitoring acceleration in a plurality of directions; and monitoring pressure variations.

According to another aspect of the present invention, a method of operating a sensor adapted to sense seismic energy with insensitivity to tilt is provided that includes providing a forced feedback compensation to the sensor.

According to another aspect of the present invention, a method of determining the tilt angle of a sensor module adapted to sense seismic energy is provided that includes providing a forced feedback compensation to the sensor; and measuring the steady-state gravity field over a predetermined time period.

According to another aspect of the present invention, a method of determining the tilt angle of a sensor module is provided that includes calibrating the sensor module to determine tilt information; storing the tilt information within the sensor module; and measuring an effect of gravity on the sensor module.

According to another aspect of the present invention, a method of manufacturing a sensor assembly having a plurality of axes of sensitivity is provided that includes minimizing cross-axis sensitivity; minimizing the tolerance of the sensitivity; and providing axes of sensitivity that are approximately orthogonal.

According to another aspect of the present invention, a method for acquiring seismic data is provided that includes coupling a seismic recorder to a sensor module including a plurality of accelerometers.

According to another aspect of the present invention, a method of determining the orientation of a 3-axis sensor is provided that includes performing a 3-dimensional measurement of a gravity field; determining a gravity vector; performing a 3-dimensional measurement of a magnetic field; determining a magnetic vector; and determining the direction of magnetic north and gravity down.

According to another aspect of the present invention, a method of sensing seismic energy is provided that includes synchronizing the operation of a seismic sensor module, and synchronizing the operation of a seismic sensor module includes using a global positioning system signal from a global positioning system receiver within the sensor module.

According to another aspect of the present invention, a method of sensing seismic energy is provided that includes determining the position of the seismic sensor, and determining the position of the seismic sensor includes using a global positioning system signal from a global positioning system receiver within the sensor module.

According to another aspect of the present invention, a method of synchronizing the acquisition of seismic data is provided that includes receiving a signal containing time information; and controlling the operation of one or more accelerometers adapted to sense seismic energy and one or more seismic recorders using the signal.

According to another aspect of the present invention, a method of determining the location of the acquisition of seismic data is provided that includes receiving a signal containing position information; and determining the position of one or more seismic sensors using the signal.

According to another aspect of the present invention, a method of determining the degree of coupling between a sensor assembly and the ground is provided that includes generating a force; recording a response of the sensor assembly to the force; and analyzing the response.

According to another aspect of the present invention, a method of determining the vector fidelity of a sensor assembly is provided that includes generating a force; recording a response of the sensor assembly to the force; and analyzing the response.

According to another aspect of the present invention, a method of determining the orientation of a sensor module, including one or more accelerometers, without direct measurement is provided that includes generating a force at a plurality of source points; recording a response of the sensor module to the force; and analyzing the response.

According to another aspect of the present invention, a method of determining the state-of-health for a sensor module, including a plurality of accelerometers and a seismic recorder, is provided that includes sending a bitstream to the sensor module; decoding, capturing, and looping-back the bitstream to the seismic recorder; and capturing and analyzing the bitstream by the seismic recorder.

According to another aspect of the present invention, a method of determining the state-of-health for a sensor assembly, including an application specific integrated chip (ASIC), coupled to a seismic recorder is provided that includes sending a bitstream to the ASIC; decoding, capturing, and looping-back the bitstream to the seismic recorder; and capturing and analyzing the bitstream by the seismic recorder.

According to another aspect of the present invention, a method of determining the state-of-health for a sensor assembly adapted to sense seismic energy, including an ASIC, is provided that includes reading contents of the ASIC; and validating the contents of the ASIC.

According to another aspect of the present invention, a method of determining the state-of-health for a sensor assembly adapted to sense seismic energy, including an accelerometer, is provided that includes operating the accelerometer; and monitoring the operation of the accelerometer. Monitoring the operation of the accelerometer includes monitoring the accelerometer for instability to indicate a malfunction of the accelerometer or an excessive external acceleration.

According to another aspect of the present invention, a method of determining the state-of-health for a sensor assembly adapted to sense seismic energy, including an accelerometer, is provided that includes exciting the accelerometer with a bitstream; and acquiring, analyzing and judging an output signal generated by the accelerometer. Judging an output signal generated by the accelerometer includes judging a magnitude of the output signal to indicate a malfunction of the accelerometer.

According to another aspect of the present invention, a method of determining the state-of-health for a sensor assembly adapted to sense seismic energy, including an accelerometer, is provided that includes exciting the accelerometer with a bitstream; and acquiring, analyzing and judging an output signal generated by the accelerometer. Judging an output signal generated by the accelerometer includes judging a phase response of the output signal to indicate a malfunction of the accelerometer.

According to another aspect of the present invention, a method of determining the state-of-health for a sensor assembly adapted to sense seismic energy, including an accelerometer, is provided that includes exciting the accelerometer with a bitstream; and acquiring, analyzing and judging an output signal generated by the accelerometer. Judging an output signal generated by the accelerometer includes judging a total harmonic distortion of the output signal to indicate a malfunction of the accelerometer.

According to another aspect of the present invention, a method of determining the state-of-health for a sensor assembly adapted to sense seismic energy, including an accelerometer, is provided that includes operating the accelerometer for a period of time; and analyzing an output signal generated by the accelerometer. Analyzing an output signal includes detecting an excessive root-mean-square amplitude response of the output signal to indicate a malfunction of the accelerometer or a noisy environment.

According to another aspect of the present invention, a method of determining the state-of-health for a sensor assembly adapted to sense seismic energy, including an accelerometer, is provided that includes operating the accelerometer; and analyzing an output signal generated by the accelerometer. Analyzing an output signal generated by the accelerometer includes analyzing an offset and a gravity cancellation magnitude of the output signal to detect a change in the inclination of the accelerometer.

According to another aspect of the present invention, a method of determining the state-of-health for a sensor assembly adapted to sense seismic energy, including three accelerometers, is provided that includes operating the accelerometers; and monitoring one or more output signals generated by the accelerometers. Monitoring one or more output signals generated by the accelerometers includes monitoring a vector sum of the self-measured coefficients of gravity of the output signals to detect a malfunction of the sensor assembly.

According to another aspect of the present invention, a method of determining the state-of-health for a sensor assembly adapted to sense seismic energy, including three accelerometers, is provided that includes operating the accelerometers; driving two of the accelerometers at a reference frequency; monitoring an output signal generated by the undriven accelerometer; and rotating through all the accelerometers. Monitoring an output signal generated by the undriven accelerometer includes monitoring the magnitude of the reference frequency in the output signal of the undriven accelerometer to detect a malfunction of the sensor assembly.

According to another aspect of the present invention, a method of determining the state-of-health for a sensor assembly adapted to sense seismic energy, including one or more accelerometers, is provided that includes operating the accelerometers for a period of time; removing DC offset from one or more output signals generated by the accelerometer to produce one or more resulting signals; transforming the resulting signals from Cartesian coordinates into polar coordinates; and analyzing the polar coordinates. Analyzing the polar coordinates includes analyzing one or more peak and root-mean-square amplitude results to indicate a malfunction of the sensor assembly or a noisy acquisition environment.

According to another aspect of the present invention, a method of determining the state-of-health for a sensor assembly adapted to sense seismic energy, including one or more accelerometers, is provided that includes (a) operating the accelerometers; (b) monitoring one or more output signals generated by the accelerometers; (c) analyzing the output signals; (d) changing the orientation of the sensor assembly; and (e) repeating steps (b), (c) and (d) for a plurality of orientations. Analyzing the output signals includes calculating the sensor's angles with respect to gravity from a vector slim of the self-measured coefficients of gravity in any orientation. Analyzing the output signals further includes analyzing the sensor's angles with respect to gravity to indicate a malfunction of the sensor assembly.

DETAILED DESCRIPTION OF THE ILLUSTRATIVE EMBODIMENTS

Figure 1:
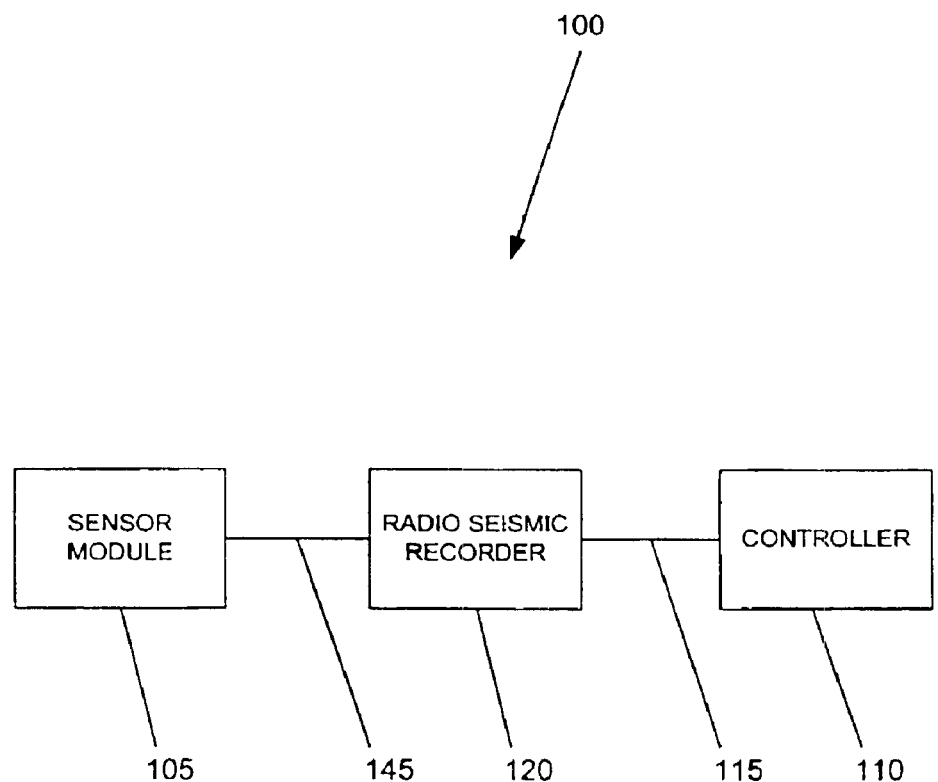
FIG. 1 is a schematic view of an embodiment of a system for acquiring seismic data.

Referring to FIG. 1, a preferred embodiment of a system 100 for sensing seismic data includes a sensor module 105, a controller 110 and a radio seismic recorder (RSR) 120. The sensor module 105 is preferably coupled to the radio seismic recorder (RSR) 120 by a communication interface 145. The controller 110 is preferably coupled to the radio seismic recorder (RSR) 120 by a communication interface 115.

Figure 2:
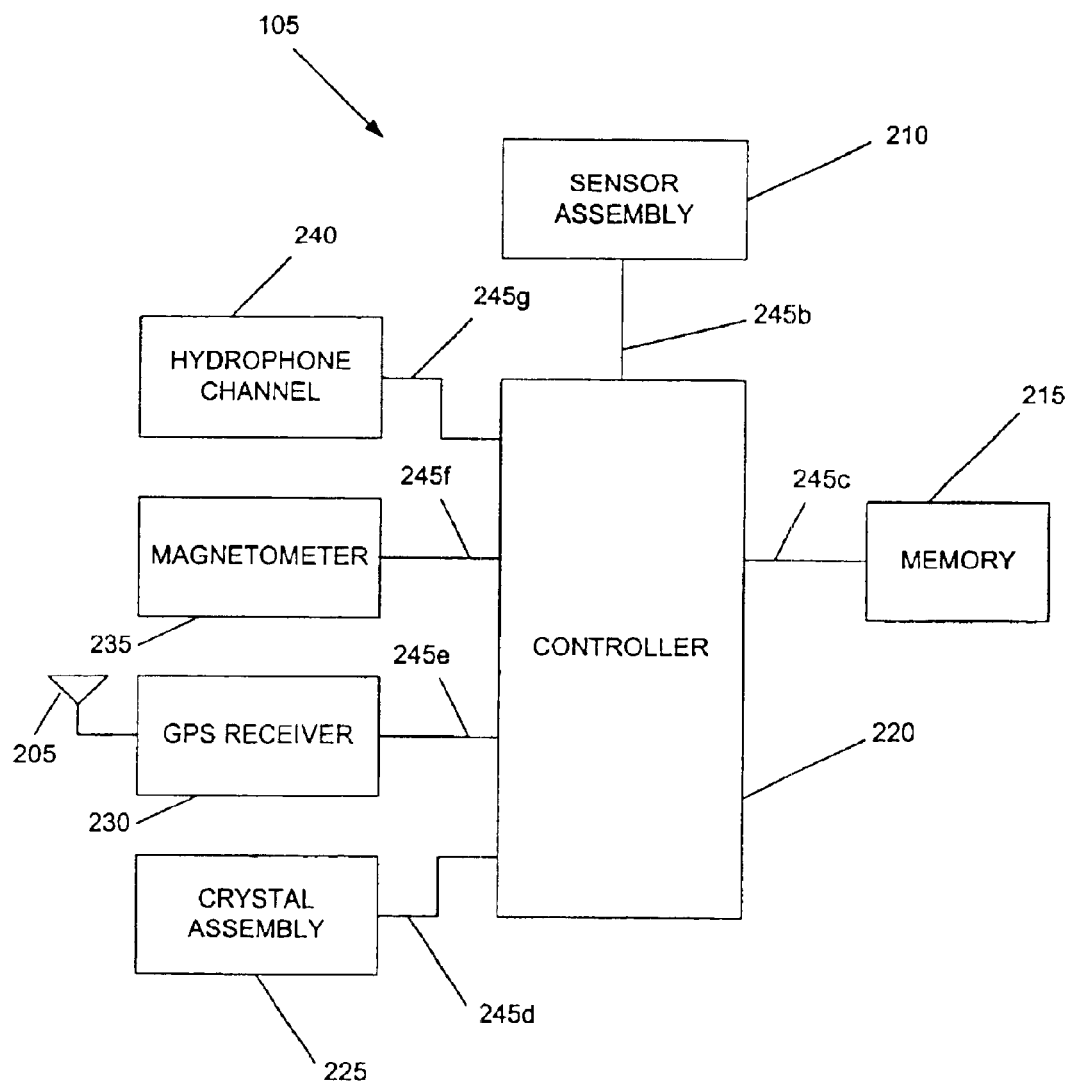
FIG. 2 is a schematic view of an embodiment of the sensor module of the system of FIG. 1.

Referring to FIG. 2, the sensor module 105 preferably includes an antenna 205, a sensor assembly 210, a memory 215, a controller 220, a crystal assembly 225, a global positioning system (GPS) receiver 230, a magnetometer 235, a hydrophone channel 240, and one or more communication interfaces 245.

The antenna 205 is preferably coupled to the GPS receiver 230. The antenna 205 may be, for example, active or passive. In a preferred embodiment, the antenna 205 is active in order to optimally provide improved signal to noise ratio.

Figure 3:
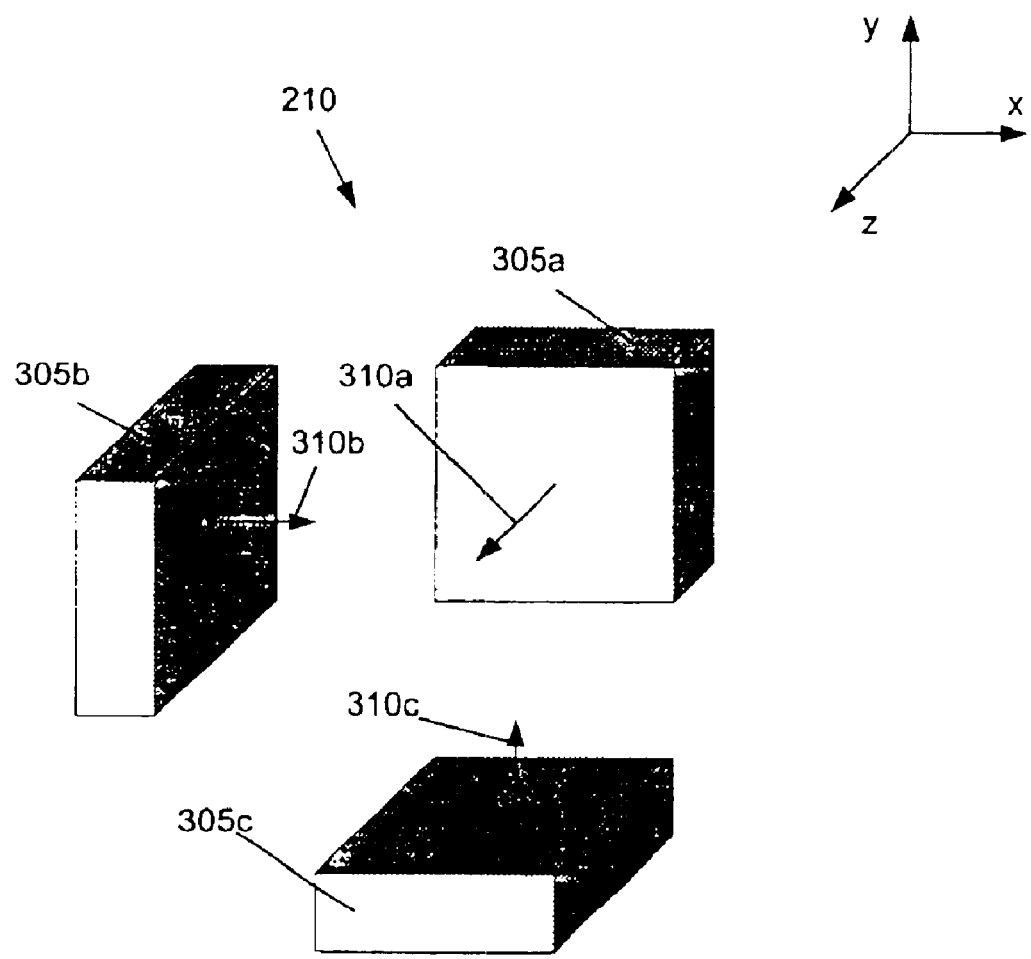
FIG. 3 is a schematic view of an embodiment of the sensor assembly of the sensor module of FIG. 2.

Referring to FIG. 3, the sensor assembly 210 preferably includes one or more accelerometers 305. The sensor assembly 210 is preferably coupled to the controller 220 by a communication interface 245b. In a preferred embodiment, the sensor assembly 210 includes a first accelerometer 305a, a second accelerometer 305b, and a third accelerometer 305c. In a preferred embodiment, each accelerometer 305 further includes one or more axes of sensitivity 310. The first accelerometer 305a preferably includes a first axis of sensitivity 310a. The first axis of sensitivity 310a is preferably approximately parallel to the z-axis. The second accelerometer 305b preferably includes a second axis of sensitivity 310b. The second axis of sensitivity 310b is preferably approximately parallel to the x-axis. The third accelerometer 305c preferably includes a third axis of sensitivity 310c. The third axis of sensitivity 310c is preferably approximately parallel to the y-axis. The axes of sensitivity 310 are preferably approximately orthogonal to each other. The sensor assembly 210 and the accelerometers 305 are preferably provided as disclosed in one or more of the following: U.S. patent application Ser. No. 09/936,634, filed on Sep. 12, 2001, and Ser. No. 09/936,640, filed on Sep. 12, 2001, the disclosures of which are incorporated herein by reference.

Figure 4:
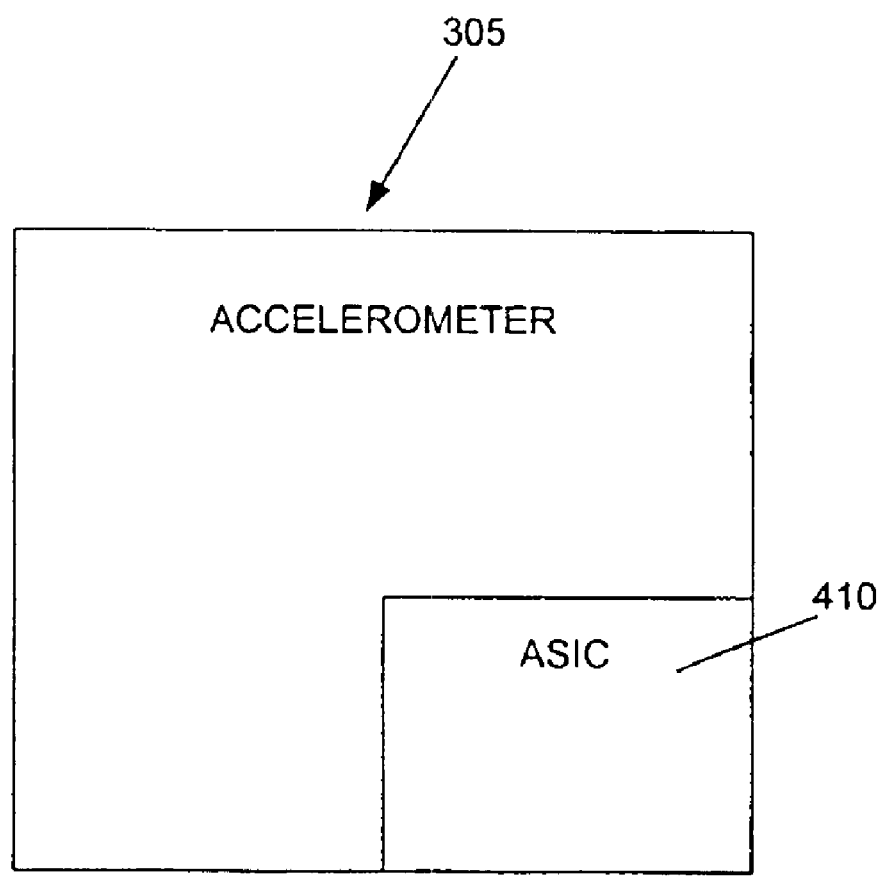
FIG. 4 is a schematic view of an embodiment of the accelerometer of the sensor assembly of FIG. 3.

Referring to FIG. 4, each accelerometer 305 preferably includes a corresponding application specific integrated circuit (ASIC) 410. Each accelerometer 305 is preferably coupled to the corresponding ASIC 410. The ASIC 410 preferably includes feedback circuitry adapted to provide force balanced feedback to the corresponding accelerometer 305. The ASIC 410 also preferably includes memory for storage of individual parameters for each corresponding accelerometer 305. The ASIC 410 also preferably includes digitization circuitry to provide for a digital output from each corresponding accelerometer 305. The ASIC 410 may be, for example, an analog integrated circuit using analog means to generate feedback and providing analog accelerometer output or a mixed signal integrated circuit using a combination of analog and digital means to generate feedback and providing digital accelerometer output. In a preferred embodiment, the ASIC 410 is preferably provided as disclosed in the following: copending U.S. patent application Ser. No. 09/936,630, filed on Sep. 14, 2001, the disclosure of which is incorporated herein by reference in order that the ASIC 410 may optimally provide resolution and tilt insensitivity for seismic sensing. The packaging of the accelerometer 305 and the ASIC 410 are preferably provided as disclosed in the following: copending U.S. patent application Ser. No. 09/936,634, filed on Sep. 12, 2001, the disclosure of which is incorporated herein by reference.

Figure 5:
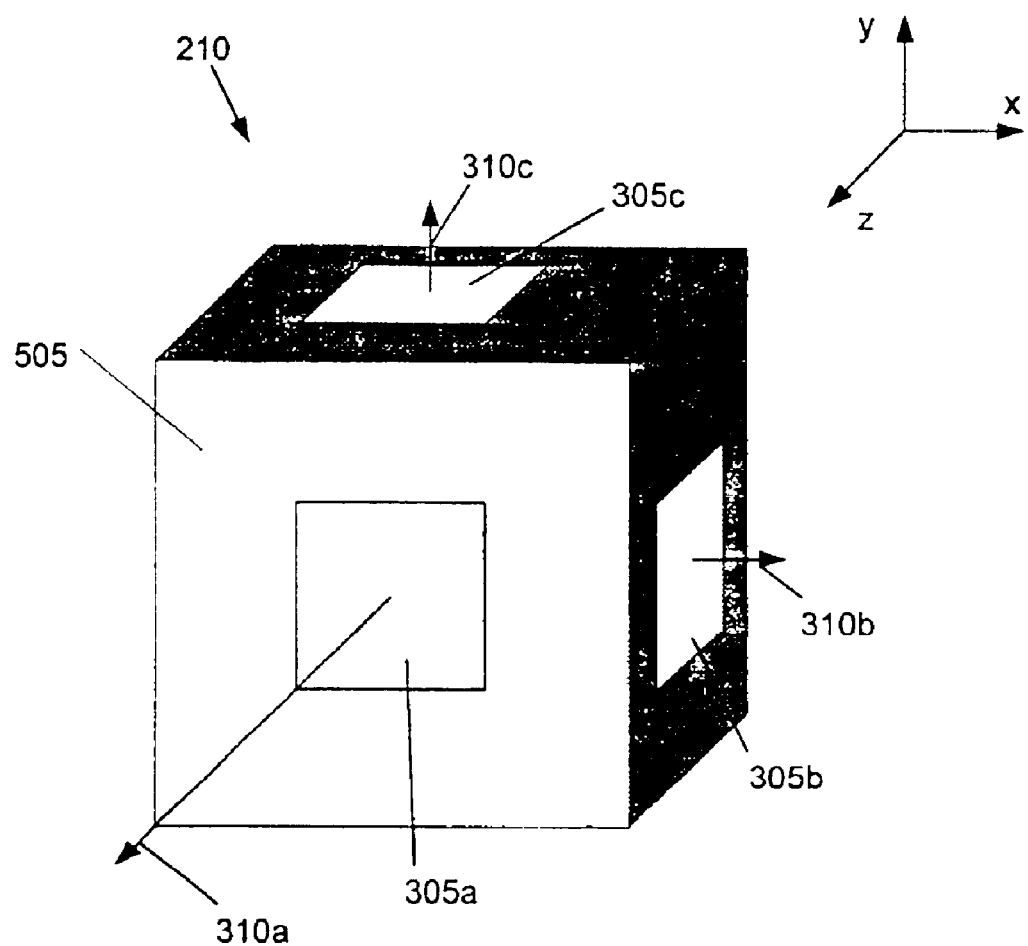
FIG. 5 is a schematic view of an alternate embodiment of the sensor assembly of the sensor module of FIG. 2.

Referring to FIG. 5, an alternate embodiment of the sensor assembly 210 further includes a monolithic package 505. The first accelerometer 305a is preferably coupled to the monolithic package 505 to maintain the first axis of sensitivity 310a substantially parallel to the z-axis. The second accelerometer 305b is preferably coupled to the monolithic package 505 to maintain the second axis of sensitivity 310b substantially parallel to the x-axis. The third accelerometer 305c is preferably coupled to the monolithic package 505 to maintain the third axis of sensitivity 310c substantially parallel to the y-axis. The axes of sensitivity 310 are preferably approximately orthogonal to each other. The packaging of the accelerometers 305 in the monolithic package 505 is preferably provided as disclosed in the following: copending U.S. patent application Ser. No. 09/936,634, filed on Sep. 12, 2001, the disclosure of which is incorporated herein by reference.

Referring again to FIG. 2, the memory 215 is preferably coupled to the controller 220 by a communication interface 245c. The memory 215 may be, for example, FLASH memory or EEPROM memory. In a preferred embodiment, the memory 215 is EEPROM memory in order to optimally provide non-volatile storage of parameters and data of the sensor module 105 at low cost. In an alternate embodiment, the memory 215 may be distributed among one or more components of the sensor module 105.

The controller 220 is preferably coupled to the sensor assembly 210 by the communication interface 245b. The controller 220 is also preferably coupled to the memory 215 by the communication interface 245c. The controller 220 is also preferably coupled to the crystal assembly 225 by a communication interface 245d. The controller 220 is also preferably coupled to the GPS receiver 230 by a communication interface 245e. The controller 220 is also preferably coupled to the magnetometer 235 by a communication interface 245f. The controller 220 is also preferably coupled to the hydrophone channel 240 by a communication 11 interface 245g. The controller 220 may be, for example, a custom integrated circuit or a micro controller. In a preferred embodiment, the controller 220 is a field programmable gate array (FPGA) in order to optimally provide reduced design cycle time and capability for future enhancements.

Figure 6:
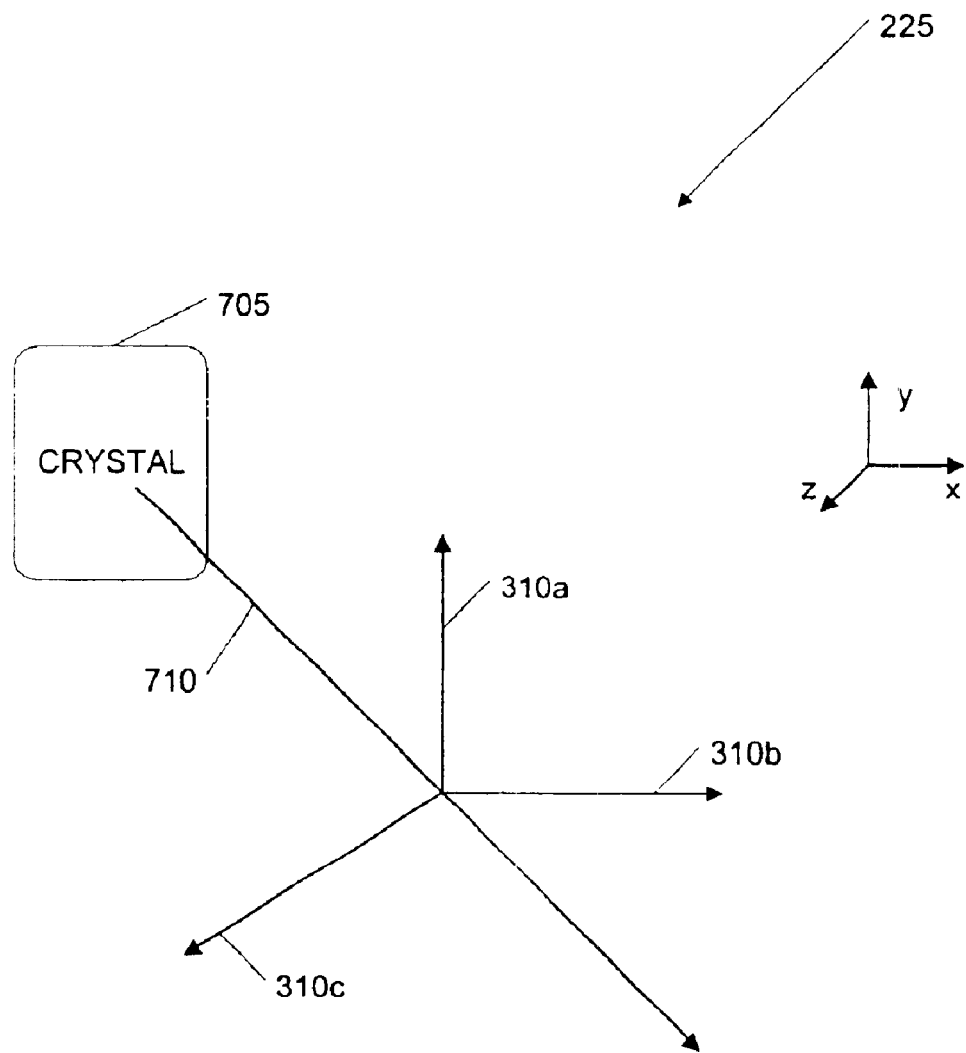
FIG. 6 is a schematic view of an embodiment of the radio seismic recorder of the system of FIG. 1.

Referring to FIG. 6, in a preferred embodiment, the crystal assembly 225 includes a piezocrystal 705. The crystal assembly 225 is preferably coupled to the controller 220 by the communication interface 245d. The piezocrystal 705 may be, for example, any conventional piezocrystal or the GeoPinger crystal, available from Input/Output Inc. In a preferred embodiment, the piezocrystal 705 is the GeoPinger crystal, available from Input/Output Inc., in order to optimally provide a force to the sensor module 105. The piezocrystal 705 preferably produces an impulse 710. In a preferred embodiment, the piezocrystal 705 is preferably adapted to produce components of the impulse 710 equally in all the axes of sensitivity 310 of the sensor assembly 210. The impulse 710 is preferably unipolar. The impulse 710 may, for example, range from about 0.5 to 5 milliseconds in duration. In a preferred embodiment, the impulse 710 ranges from about 0.5 to 1 millisecond in order to optimally provide a sharp impulse.

Figure 7:
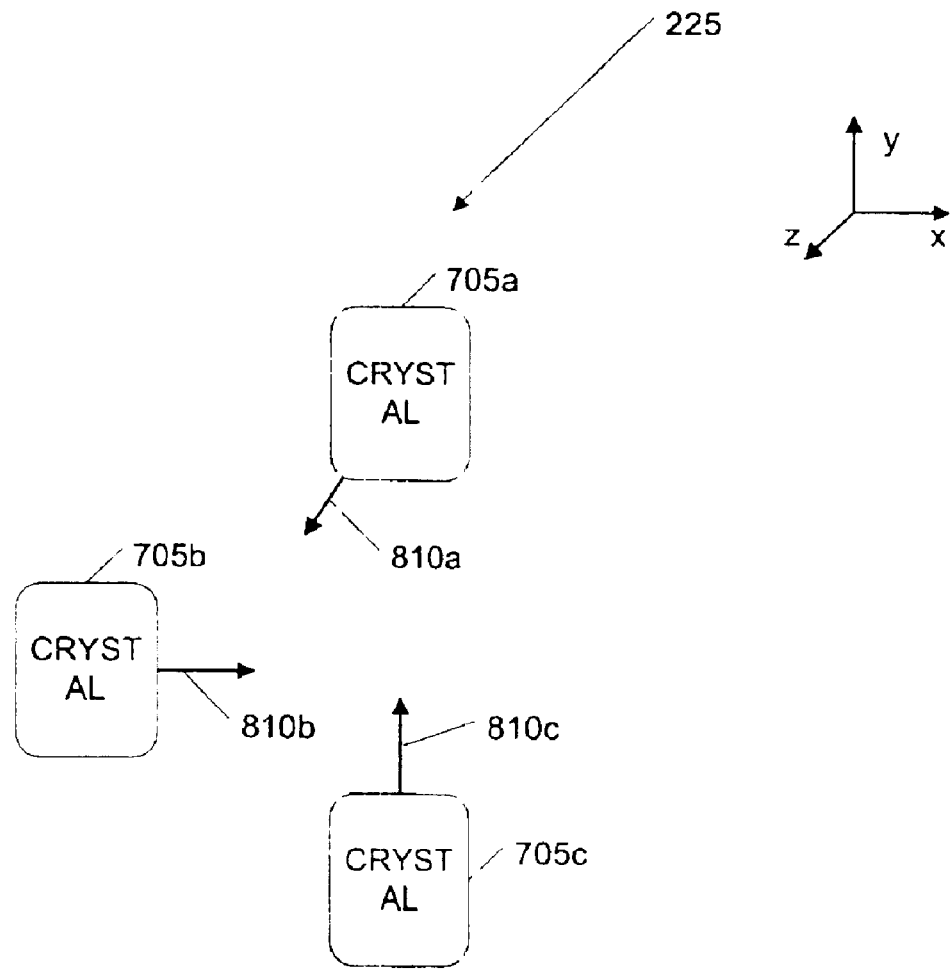
FIG. 7 is a schematic view of an embodiment of the crystal assembly of the sensor module of FIG. 2.

Referring to FIG. 7, in an alternate embodiment, the crystal assembly 225 includes a plurality of piezocrystals 705. The number of piezocrystals 705 preferably corresponds to the number of accelerometers 305 in the sensor assembly 210. In a preferred embodiment, there is a first piezocrystal 705a, a second piezocrystal 705b, and a third piezocrystal 705c. The piezocrystals 705 preferably produce one or more impulses 810. The first piezocrystal 705a is preferably adapted to produce a first impulse 810a that is applied substantially parallel to the first axis of sensitivity 310a of the sensor assembly 210. The second piezocrystal 705b is preferably adapted to produce a second impulse 810b that is applied substantially parallel to the second axis of sensitivity 310b of the sensor assembly 210. The third piezocrystal 705c is preferably adapted to produce a third impulse 810c that is applied substantially parallel to the third axis of sensitivity 310c of the sensor assembly 210. The impulses 810 are preferably unipolar. The impulses 810 may, for example, range from about 0.5 to 5 milliseconds in duration. In a preferred embodiment, the impulses 810 range from about 0.5 to 1 millisecond in order to optimally provide a sharp impulse.

Referring again to FIG. 2, the GPS receiver 230 is preferably coupled to the controller 220 by the communication interface 245e. The GPS receiver 230 may be any commercially available GPS receiver. In a preferred embodiment, the GPS receiver 230 is the μ-Blox GPSMS 1 receiver module in order to optimally provide reduced sensor module size.

The magnetometer 235 is preferably coupled to the controller 220 by the communication interface 245f. The magnetometer 235 may be, for example, a flux gate or a magneto-resistive device. The magnetometer 235 is preferably a 3-axis magnetometer.

The hydrophone channel 240 is preferably coupled to the controller 220 by the communication interface 245g. The hydrophone channel 240 preferably includes one or more hydrophones. In a preferred embodiment, the hydrophone channel 240 further includes circuitry, such as an amplifier and an analog-to-digital converter, adapted to handle and digitize one or more signals from the hydrophones. The hydrophones may be, for example, any commercially available hydrophone. In a preferred embodiment, the hydrophone channel 240 is spectral shaped as disclosed in the following: copending U.S. patent application Ser. No. 09/913,753, filed on Nov. 19, 2001, the disclosure of which is incorporated herein by reference, in order to optimally provide a frequency response matched to the sensor module 105 accelerometers 305.

The communications interfaces 245 may be implemented using any conventional communications techniques. The communications interfaces 245 may be, for example, radio links, fiber optics, or inductively coupled. In a preferred embodiment, the communications interfaces 245 are implemented as traces on printed circuit boards in order to provide functionality at a low cost.

Referring again to FIG. 1, the controller 110 is preferably coupled to the radio seismic recorder 120 by a communication interface 115. The controller 110 preferably provides instructions and timing to the radio seismic recorder 120. The controller 110 also preferably receives data and status from the radio seismic recorder 120. The controller 110 may be any conventional device adapted to control the radio seismic recorder 120, for example, the Input/Output OCR or the Input/Output System 2000. In a preferred embodiment, the controller 110 is the Input/Output System 2000.

The communication interface 115 may be, for example, wire, printed circuit board trace or other conductors, optical fiber or other optical coupling, radio, or may be circuit or packet switched networks. In a preferred embodiment, the communication interface 115 is radio in order to simplify system 100 deployment.

Figure 8:
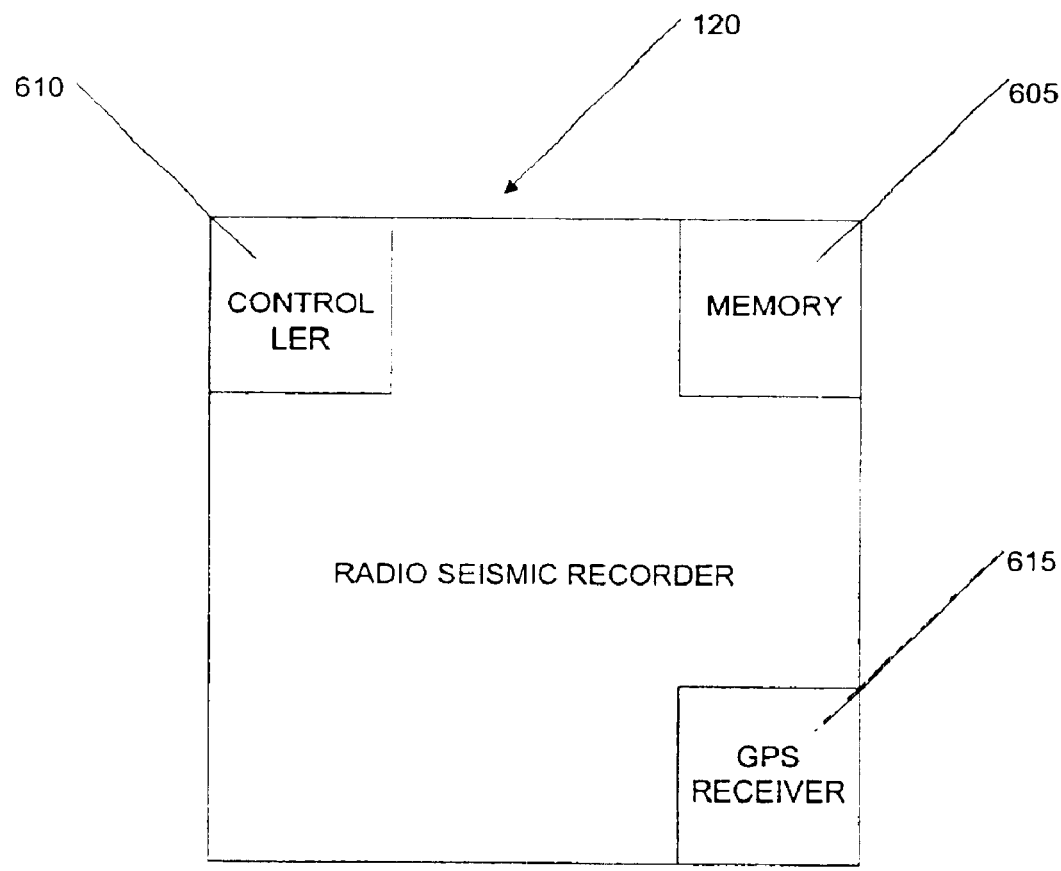
FIG. 8 is a schematic view of an alternate embodiment of the crystal assembly of the sensor module of FIG. 2.

Referring to FIG. 8, in a preferred embodiment, the radio seismic recorder (RSR) 120 includes a memory 605, a controller 610, and a GPS receiver 615. The RSR 120 is preferably coupled to the sensor module 105 by the communication interface 145. The RSR 120 may be, for example, a cable interface unit that allows transmission of seismic data on a high bandwidth conductor or optical fiber cable, a radio interface unit to transmit the seismic data, or an autonomous or semi-autonomous recorder. In a preferred embodiment, the RSR 120 is the Remote Seismic Recorder manufactured by Input/Output Inc.

The memory 605 is preferably coupled to the RSR 120. The memory 605 may be, for example, hard disk or other non-volatile storage medium of suitable capacity. In a preferred embodiment, the memory 605 is FLASH memory in order to optimally provide low power and non-volatile storage.

The controller 610 is preferably coupled to the RSR 120. The controller 610 may be, for example, programmable logic devices or a custom integrated circuit. In a preferred embodiment, the controller 610 is a microprocessor in order to optimally provide addition of features and simplified development.

The GPS receiver 615 is preferably coupled to the RSR 120. The GPS receiver 615 may be, for example, any commercially available GPS receiver. In a preferred embodiment, the GPS receiver 615 is the μ-Blox GPSMS 1 receiver module in order to optimally provide product miniaturization.

The communication interface 145 preferably transfers data and status information from the sensor module 105 to the RSR 120. The communication interface 145 preferably further transfers instructions, power and timing information from the RSR 120 to the sensor module 105. The communication interface 145 may be, for example, wire, printed circuit board trace or other conductors, optical fiber or other optical coupling, or radio. In a preferred embodiment, the communication interface 145 is wire.

In an alternate embodiment, the communication interface 145 is printed circuit board trace and the sensor module 105 is integrated with the radio seismic recorder 120.

In an alternate embodiment, the sensor module 105 may be a fully or partially autonomous sensor module 105 which contains a seismic data acquisition and recording system.

In an alternate embodiment, the sensor module 105 may be coupled to or integrated with a telemetry device employing radio, wire or other conductive media, or optical fiber for transmission of seismic data acquired from the sensor module 105.

In an alternate embodiment, the system 100 has a plurality of sensor modules 105 and a plurality of radio seismic recorders 120.

Figure 9A:
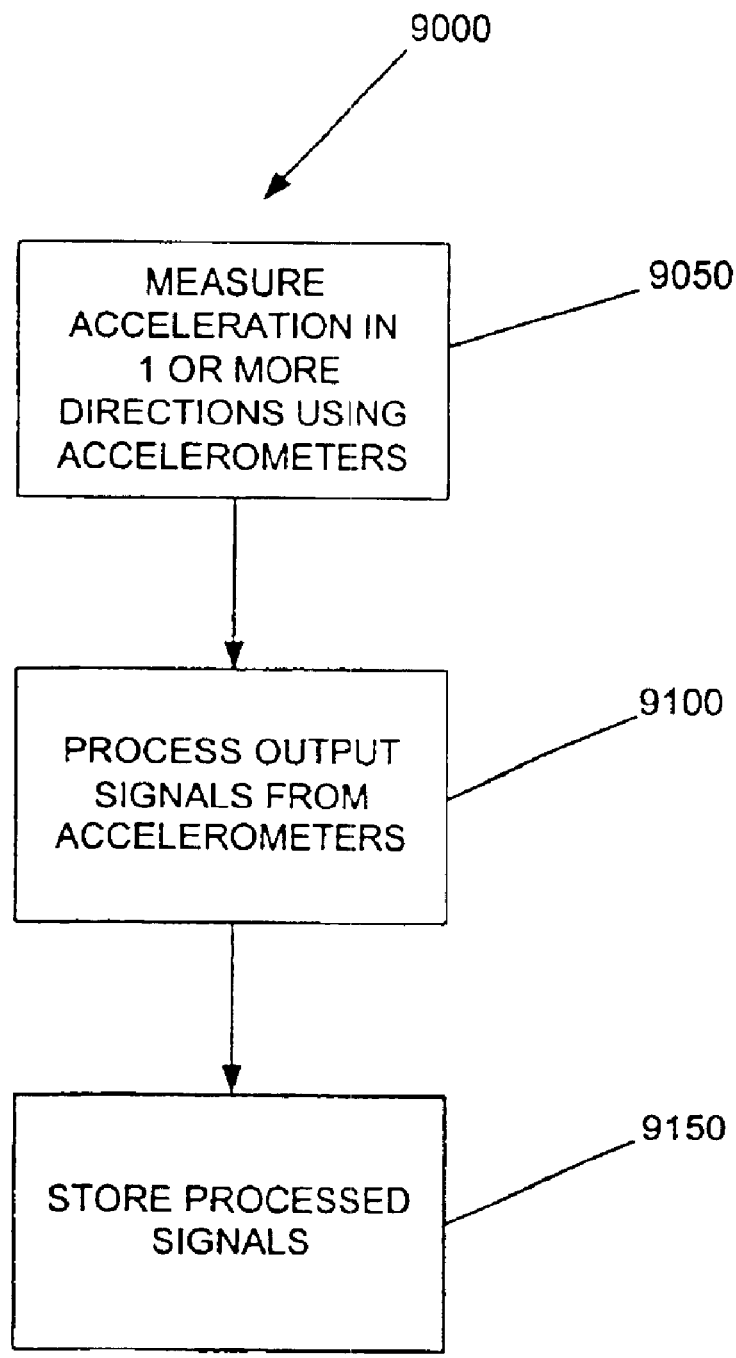
FIG. 9A is a block diagram of an embodiment of a method for acquiring seismic data using the system of FIG. 1.

Referring to FIG. 9A, a preferred embodiment of a method 9000 for sensing 29 seismic energy using the system 100 includes: (1) measuring acceleration in one or more directions using accelerometers 305 in step 9050; (2) processing one or more output signals from the accelerometers 305 in step 9100; and (3) storing the processed signals in step 9150. Seismic energy may be, for example, characterized by displacement, velocity, or acceleration of ground movement. In a preferred embodiment, seismic energy is characterized by the acceleration of ground movement in order to increase sensitivity to higher frequencies.

In step 9050, one or more accelerometers 305 preferably generate output signals proportional to the component of the acceleration vector that is parallel to the corresponding axis of sensitivity 310. The output signals from the accelerometers 305 are preferably transferred to the controller 220 via the communication interface 245b.

In step 9100, the controller 220 preferably processes the output signals from the accelerometers 305 into processed signals. The processing may be, for example, transferring the signals to a storage media, or involving filters, corrections, or transformations of the signals into other coordinate systems.

In step 9150, the controller 220 preferably stores the processed signals in the storage media. In an alternate embodiment, the controller 220 transfers the processed signals to the radio seismic recorder 120 to be stored in the storage media. The storage media may be any conventional type of storage media, such as hard drives or magnetic tape. In a preferred embodiment, the storage media is flash memory in order to provide reliable operation in harsh environments.

Figure 9B:
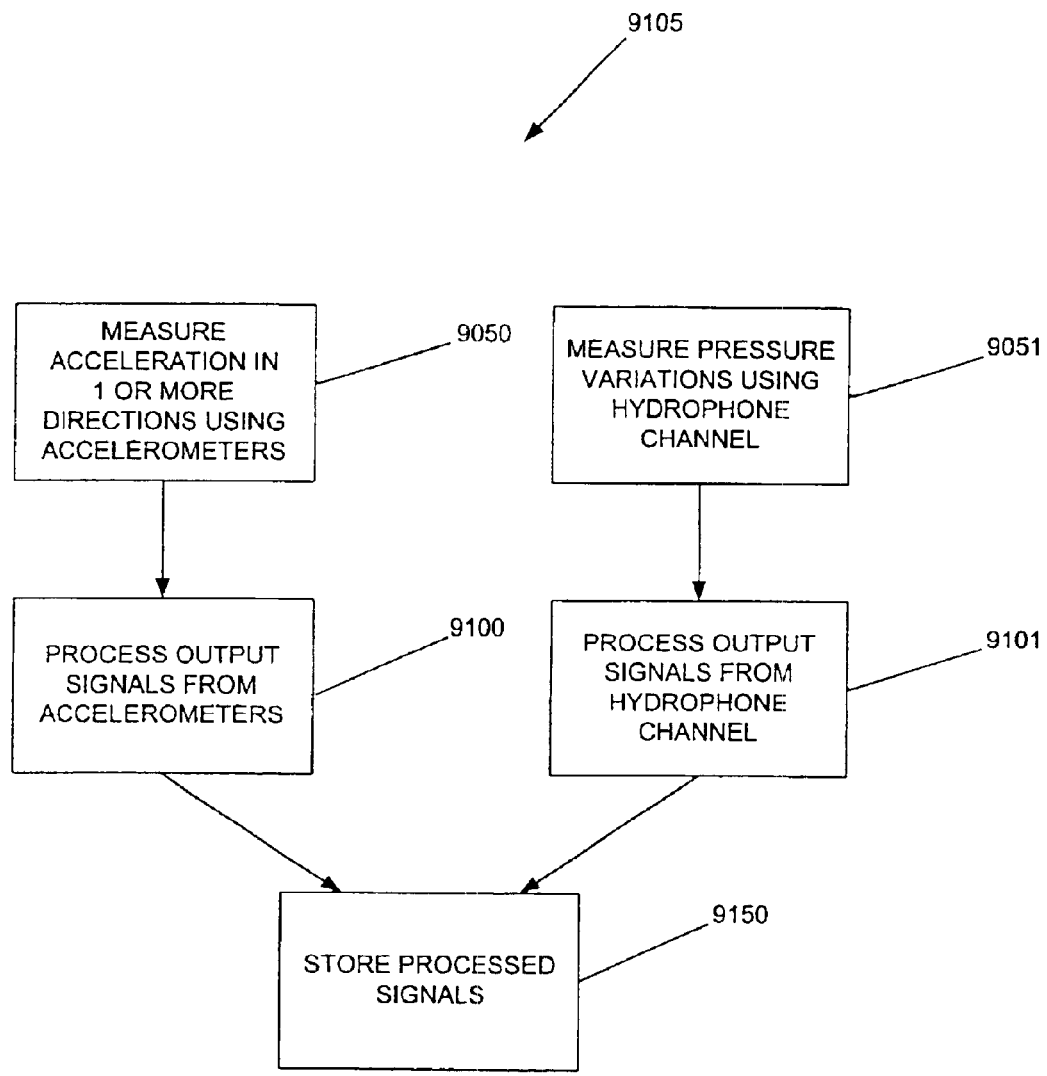
FIG. 9B is a block diagram of an alternate embodiment of a method for acquiring seismic data using the system of FIG. 1.

Referring to FIG. 9B, an alternate embodiment of a method 9105 for sensing seismic energy using the system 100 includes: measuring acceleration in one or more directions using accelerometers in step 9050; processing one or more output signals from the accelerometers in step 9100; measuring pressure variations from the hydrophone channel 240 in step 9051; processing one or more output signals from the hydrophone channel 240 in step 9101; and storing the processed signals from the hydrophone channel 240 and the accelerometers 305 in step 9150. Steps 9050 and 9051 are preferably performed simultaneously and in parallel so that the acceleration measurements are taken over the same time period as the pressure measurements. Steps 9100 and 9101 may be performed simultaneously and in parallel so that the acceleration measurements are processed over the same time period as the pressure measurements.

In step 9051, the hydrophone channel 240 measures pressure variations. The hydrophone channel 240 preferably produces one or more output signals from which changes in water pressure can be derived. The output signals from the hydrophone channel 240 are preferably transferred to the controller 220 via the communication interface 245g. The output signals may be transferred using any number of conventional transfer methods. The output signals from the hydrophone channel 240 may be used to de-ghost the accelerometer data in a conventional manner. Ghosts may occur in underwater seismic acquisition and are caused by water-column reverberations. The water-column reverberations are caused by reflections at the surface and at the bottom of the water.

In step 9101, the controller 220 preferably processes one or more output signals from the hydrophone channel 240. The processing may be, for example, transferring the output signals to the storage media, or may involve filters, corrections, or transformations of the output signals into other coordinate systems.

Figure 10:
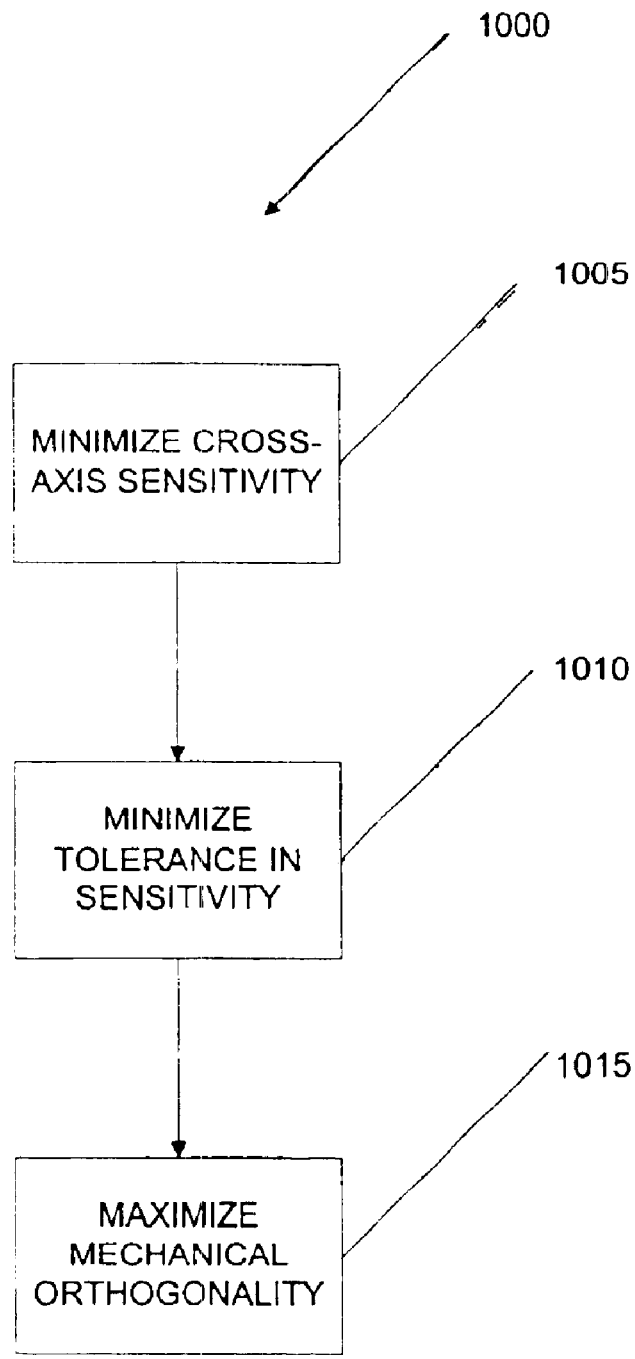
FIG. 10 is a block diagram of an embodiment of a method for manufacturing the sensor assembly of FIG. 2 to provide enhanced vector fidelity.

Referring to FIG. 10, a preferred embodiment of a method 1000 for manufacturing the sensor assembly 210 with a vector fidelity uncertainty less than about 1% includes: (1) minimizing cross-axis sensitivity in step 1005; (2) minimizing tolerance in sensitivity in step 1010; and (3) maximizing orthogonality in step 1015. Vector fidelity is a measure of the ability of the sensor assembly 210 to accurately measure the magnitude and direction of motion in three (orthogonal) directions.

Any multi-component sensor will measure an actual vector and produce for its measurement a measured vector. The error vector of any measurement is the difference between the actual vector and the measured vector. The vector fidelity uncertainty of a measurement is the magnitude of the error vector divided by the magnitude of the actual vector. The vector fidelity uncertainty of a multi-component sensor is the maximum of the vector fidelity uncertainty of measurements taken over all actual vector directions. The vector fidelity of a multi-component sensor equals one minus the vector fidelity uncertainty of the sensor. The magnitude of a vector, for any vector in Cartesian coordinates, equals the square root of the summation of the squares of its components. In a preferred embodiment, the multi-component sensor is a three-component accelerometer that measures actual accelerations to produce measured accelerations. Vector fidelity uncertainty of a multi-component sensor preferably is determined using actual vectors that have a magnitude substantially larger than the random noise added by the multi-component sensor, but not so large that the multi-component sensor becomes overloaded or saturated.

In step 1005, the sensor assembly 210 may be manufactured with the cross axis sensitivity specification of the accelerometers 305 ranging, for example, from about 0.01 to 10%. The cross-axis sensitivity of the accelerometer 305 is the magnitude of the response of the accelerometer 305 to a stimulus acting perpendicular to the axis of sensitivity 310 of the accelerometer 305 divided by the magnitude of the response of the accelerometer 305 to a stimulus of the same magnitude but acting parallel to the axis of sensitivity 310 of the accelerometer 305. In a preferred embodiment, the accelerometers 305 are manufactured with the cross axis sensitivity specification of the accelerometers 305 ranging from about 0.1 to 1% in order to provide high vector fidelity during operation of the sensor assembly 210.

In step 1010, the sensor assembly 210 may be manufactured with the tolerance in sensitivity of the sensor assembly 210 ranging, for example, from about 0.01 to 10%. In a preferred embodiment, the sensor assembly 210 is operated with the tolerance in sensitivity of the sensor assembly 210 ranging from about 0.1 to 1% in order to optimally provide high vector fidelity during operation of the sensor assembly 210.

In step 1015, the sensor assembly 210 is preferably manufactured with the axes of sensitivity 310 of the sensor assembly 210 being substantially orthogonal to provide high vector fidelity during operation of the sensor assembly 210.

The fabrication of the sensor assembly 210 with a vector fidelity uncertainty less than about 1% is preferably provided as disclosed in the following: copending U.S. patent application Ser. No. 09/936,634, filed on Sep. 12, 2001, the disclosure of which is incorporated herein by reference.

Figure 11:
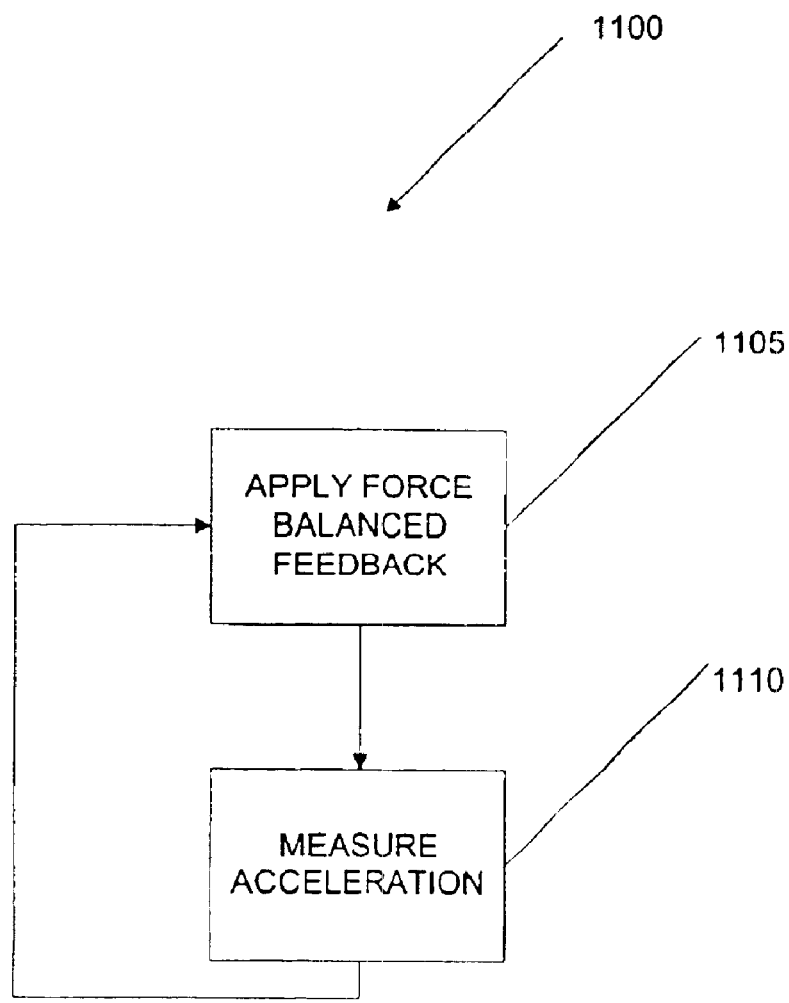
FIG. 11 is a block diagram of an embodiment of a method for operating the sensor assembly of FIG. 2 to provide insensitivity to tilt.

Referring to FIG. 11, a preferred embodiment of a method 1100 for operating the sensor assembly 210 with insensitivity to tilt includes: (1) applying a separate force balanced feedback to each accelerometer 305 in step 1105; and (2) measuring acceleration in step 1110. The sensor assembly 210 is deemed insensitive to tilt if the quality of performance of the sensor assembly 210 is essentially the same at any fixed orientation.

In step 1105, each accelerometer 305 has an associated feedback control circuit that provides force balanced feedback to the accelerometer 305. The force balanced feedback may be provided using any number of conventional methods for providing force balanced feedback. In a preferred embodiment, the force balanced feedback holds the accelerometer 305 in a substantially fixed position in order to optimally provide sensing linearity. In a preferred embodiment, the force balanced feedback is provided by electrostatic forcing in order to optimally provide repeatable forcing. The force balanced feedback preferably overcomes the gravitational effects on the accelerometers 305 making the accelerometers 305 insensitive to tilt.

The feedback control circuit and the operation of the feedback control circuit are preferably provided as disclosed in the following: copending U.S. patent application Ser. No. 09/936,634, filed on Sep. 14, 2001, the disclosure of which is incorporated herein by reference.

In step 1110, the accelerometers 305 preferably measure acceleration along three orthogonal axes. Output signals from the accelerometers 305 preferably correspond to the acceleration measured by the accelerometers 305. The output signals from the first accelerometer 305a, the second accelerometer 305b, and the third accelerometer 305c are preferably transferred to the controller 220 via the communication interface 245b. The controller 220 may use any number of conventional methods to process the output signals from the accelerometers 305 into signals representing the full vector field of the ground motion. In a preferred embodiment, the controller 220 transfers the accelerometer 305 output signals to the radio seismic recorder 120 in order to simplify the sensor module 105 hardware. The radio seismic recorder 120 preferably scales the signals of each accelerometer 305 by a number which is inversely proportional to the factory-measured sensitivity of each accelerometer 305. Scaling the signals preferably produces data which has minimal sensitivity variation between the accelerometers 305. The minimal sensitivity variation between the accelerometers 305 preferably improves the vector fidelity of the sensor assembly 210. The acceleration measured in step 1110 is preferably used to modify the force used for force balanced feedback in step 1105. The force balanced feedback preferably cancels the externally generated accelerations on the sensor module 105 making the sensor module 105 preferably insensitive to tilt. Externally generated accelerations include gravity and acceleration caused by motion of the sensor module 105.

Figure 12:
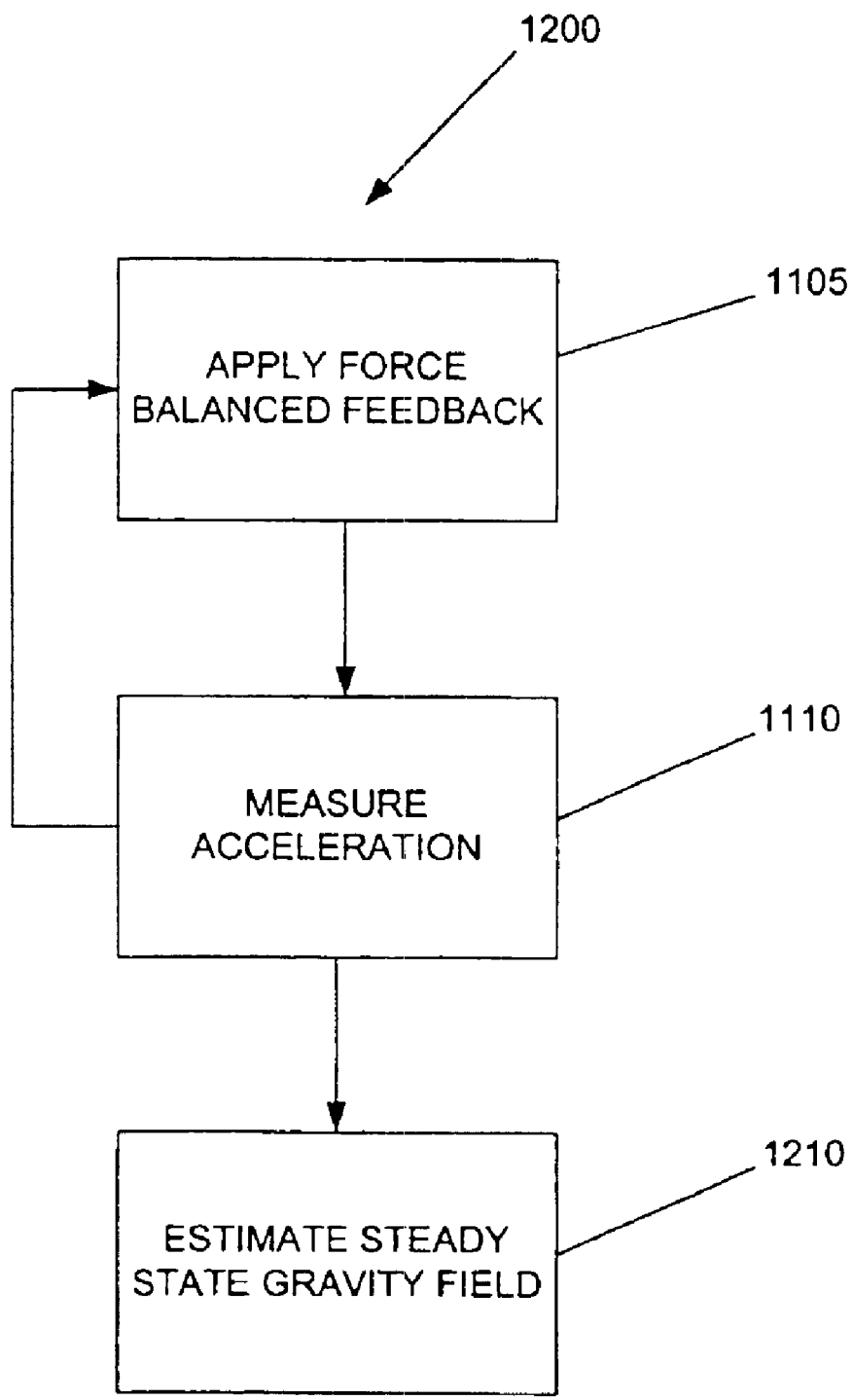
FIG. 12 is a block diagram of an embodiment of a method for determining the tilt angle of the sensor module of FIG. 1.

Referring to FIG. 12, a preferred embodiment of a method 1200 for measuring the tilt angle of the sensor module 105 preferably includes: (1) applying a separate force balanced feedback to each accelerometer 305 in step 1105; (2) measuring acceleration in step 1110; and (3) estimating the steady-state gravity field over a period of time from the measured accelerations in step 1210.

In step 1210, the steady-state gravity field acting on the sensor module 105 is preferably estimated from the acceleration measurements of step 1110 over a period of time. The steady-state gravity field may be estimated from the acceleration measurements using any number of conventional methods to estimate steady-state gravity fields. In a preferred embodiment, the sensor module 105 estimates the steady-state gravity field using the average acceleration over the period of time in order to provide a gravity estimate with reduced sensitivity to high frequency motion. The period of time may range, for example, from about 250 microseconds to 1 year. In a preferred embodiment, the period of time ranges from about 0.5 to 1 second in order to provide a relatively quick measurement that also has sufficient estimation quality. In a preferred embodiment, in step 1210, the sensor module 105 further predicts the inclination of the sensor module 105 to the Earth's gravitational force. The inclination of the sensor module 105 to the Earth's gravitational force may be estimated using any number of conventional methods to estimate the inclination of an object to the Earth's gravitational force. In a preferred embodiment, the inclination of the sensor module 105 to the Earth's gravitational force is estimated by calculating the angle between the steady-state gravity field estimate and a reference direction. The reference direction is a fixed direction relative to the sensor module 105. In a preferred embodiment, the reference direction is parallel to the major axis of the sensor module 105, which runs from the top to the bottom of the sensor module 105. In a preferred embodiment, the sensor module 105 is roughly axially symmetric about its major axis.

Figure 13:
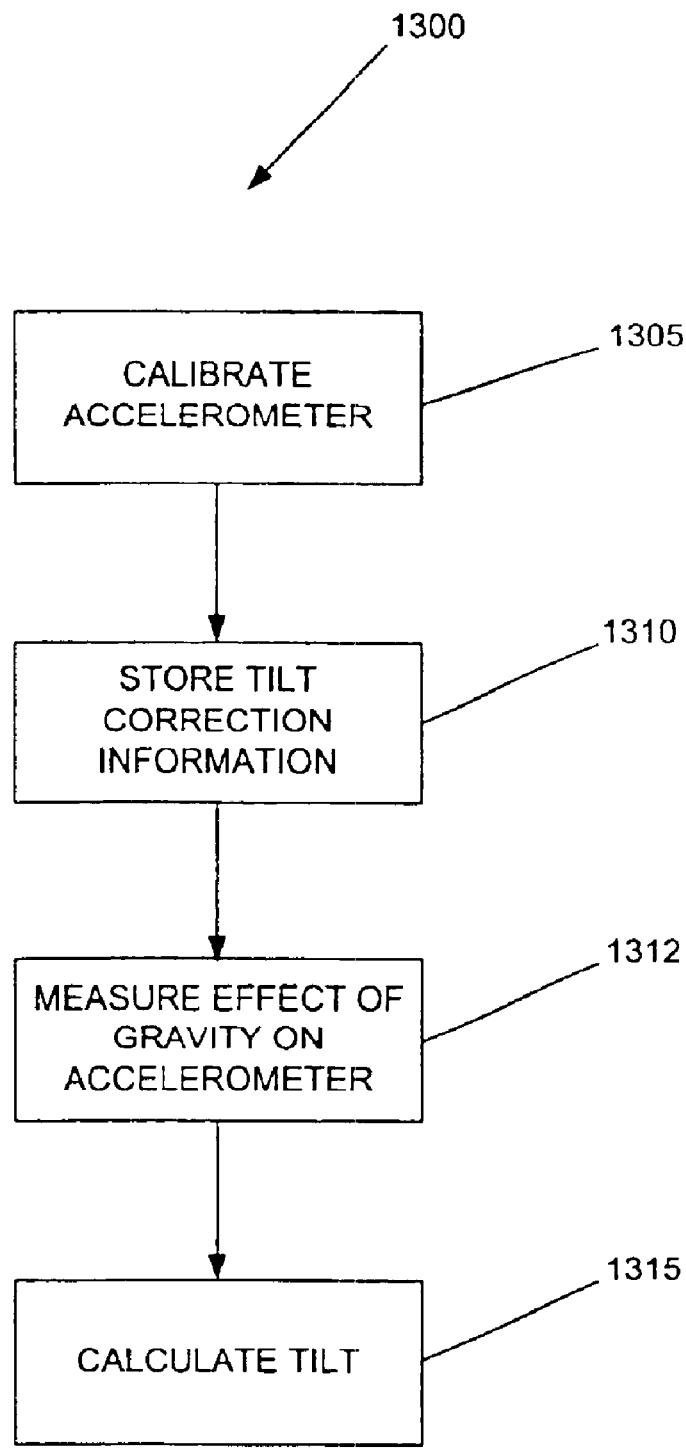
FIG. 13 is a block diagram of an alternate embodiment of a method for determining the tilt angle of the sensor module of FIG. 1.

Referring to FIG. 13, an alternate embodiment of a method 1300 for measuring the tilt angle of the sensor module 105 preferably includes: (1) calibrating the accelerometers 305 in step 1305; (2) storing tilt correction information derived from calibration in step 1310; (3) measuring the effect of gravity on the accelerometers 305 in step 1312; and (4) calculating tilt in step 1315.

In step 1305, the accelerometers 305 are preferably calibrated. Calibration of the accelerometers 305 preferably provides tilt correction information. Tilt correction information is derived by measuring a parameter of the accelerometers 305 which changes as the inclination of the accelerometers 305 changes. The parameter may be, for example, capacitance, voltage, or any other parameter that changes with the inclination of the accelerometer 305 and is useful for predicting inclination after calibration is complete. The accelerometers 305 may be calibrated using any number of conventional calibration methods. In a preferred embodiment, the accelerometers 305 are calibrated by recording the parameter's response to a 1G field at a number of known inclinations in order to optimally provide a data set for approximating the accelerometers 305 tilt.

In step 1310, tilt correction information for each accelerometer 305 from step 1305 is preferably stored to the memory 215 of the corresponding accelerometer 305.

In step 1312, the sensor module 105 is preferably operated and a measurement is made of the effect of gravity on each accelerometer 305. The measurement may be of any conventional parameter which is directly or indirectly affected by the inclination of each accelerometer 305 in the gravity field. In a preferred embodiment, the parameter measured is the same parameter measured to provide tilt correction information in step 1305.

In step 1315, the inclination of each accelerometer 305 to the Earth's gravitational force is preferably calculated. The inclination of each accelerometer 305 to the Earth's gravitational force may be estimated using any number of conventional methods to estimate the inclination of an object to the Earth's gravitational force. In a preferred embodiment, the inclination of each accelerometer 305 to the Earth's gravitational force is estimated by performing an interpolation using the parameter measured in step 1312 and the tilt correction values obtained during calibration in step 1305 in order to provide reasonable values at inclinations other than the ones used in step 1305. The inclination of the sensor module 105 is preferably estimated using accelerometer 305 inclination measurements and the known orientation of each accelerometer 305 within the sensor module 105.

Figure 14:
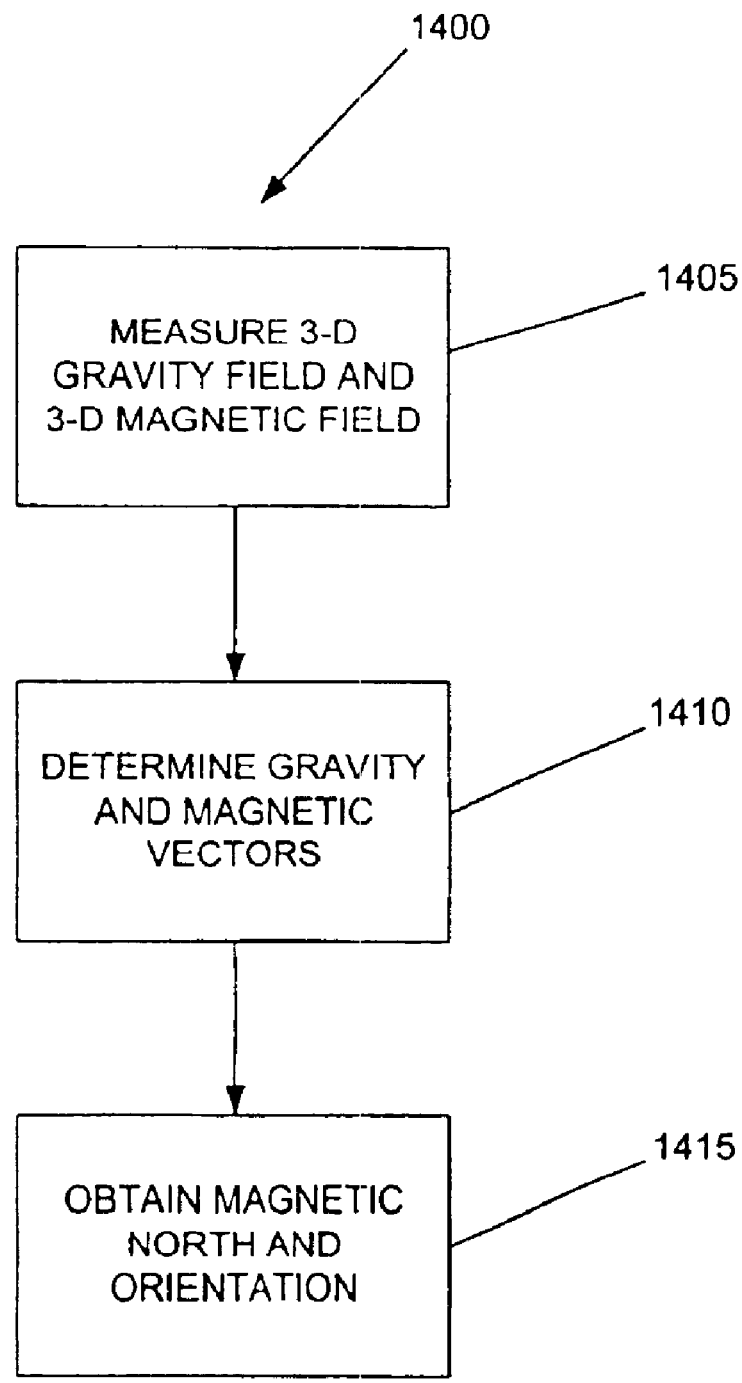
FIG. 14 is a block diagram of an embodiment of a method for determining the orientation of the sensor module of FIG. 1.

Referring to FIG. 14, a preferred embodiment of a method 1400 for determining the orientation of the sensor module 105 preferably includes: (1) performing a 3-D measurement of the gravity field and the Earth's magnetic field in step 1405; (2) determining a gravity vector and a magnetic vector in step 1410; and (3) obtaining magnetic north and gravity down directions in step 1415.

In step 1405, the sensor assembly 210 preferably measures a 3-D gravity field of the sensor module 105 and the magnetometer 235 preferably measures a 3-D magnetic north field. The magnetometer 235 may measure the 3-D magnetic north field using any number of conventional measuring methods. In a preferred embodiment, the magnetometer 235 measures the 3-D magnetic north field using a gimbal free flux gate in order to optimally provide accuracy at reduced cost.

In a preferred embodiment, in step 1405, the accelerometers 305 further transfer the 3-D gravity field data. The accelerometers 305 preferably transfer the 3-D gravity field data to the controller 220 using any number of conventional transfer methods. In a preferred embodiment, the accelerometers 305 transfer the 3-D gravity field data to the controller 220 using a polled serial interface in order to optimally provide reduced system 100 size and cost. In a preferred embodiment, in step 1405, the controller 220 further transfers the 3-D gravity field data to the radio seismic recorder 120.

In a preferred embodiment, in step 1405, the magnetometer 235 further transfers the 3-D magnetic north field data to the controller 220 using any number of conventional transfer methods. In a preferred embodiment, in step 1405, the controller 220 further transfers the 3-D magnetic north field data to the radio seismic recorder 120.

In step 1410, the radio seismic recorder 120 preferably calculates a gravity vector from the 3-D gravity field data obtained in step 1405 and a magnetic vector from the 3-D magnetic north field data obtained in step 1405. In a preferred embodiment, the gravity and magnetic vectors are calculated using projection to reduce ambiguity inherent in each measurement.

In step 1415, the radio seismic recorder 120 preferably determines magnetic north and the orientation of the sensor module 105 from the gravity and magnetic vectors calculated in step 1410.

Figure 15:
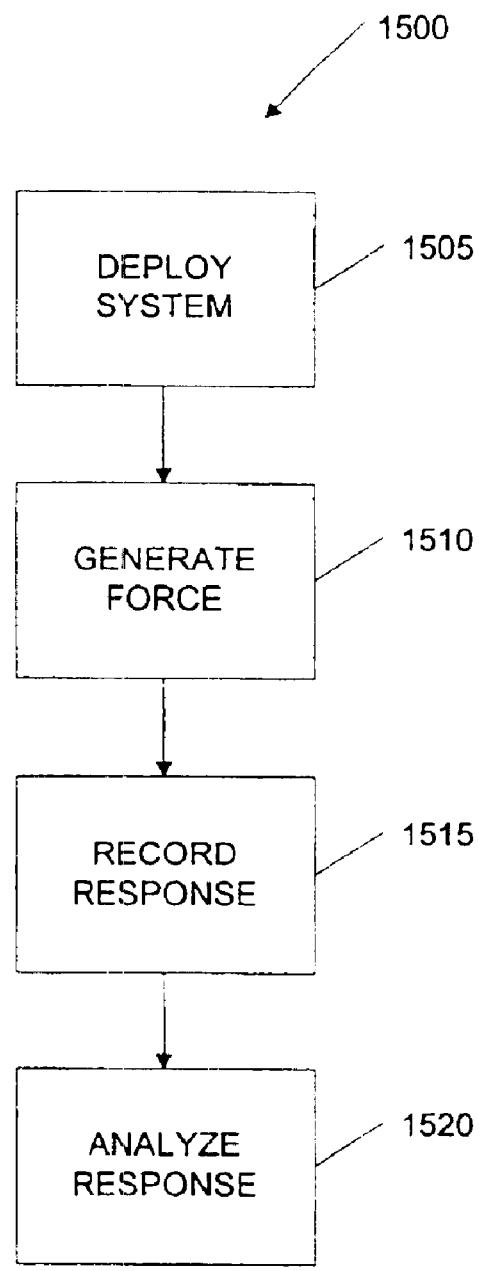
FIG. 15 is a block diagram of an embodiment of a method for determining the ground-coupling of the sensor module of FIG. 1.

Referring to FIG. 15, a preferred embodiment of a method 1500 for determining the case-ground coupling of the sensor module 105 includes: (1) deploying the sensor module 105 in step 1505; (2) generating a force in step 1510; (3) recording a response in step 1515; and (4) analyzing the response in step 1520.

In step 1505, the sensor module 105 is preferably deployed beneath the Earth's surface. In an alternate embodiment, the sensor module 105 is deployed mostly beneath the Earth's surface. The sensor module 105 may be deployed using any number of conventional deployment methods. In a preferred embodiment, the sensor module 105 is deployed in a shallow tight fitting hole in order to optimally provide coupling and noise reduction.

In step 1510, the crystal assembly 225 generates one or more forces. In a preferred embodiment, the forces are the impulse 710. In an alternate embodiment, the forces are the impulses 810. The forces may be generated using any number of conventional force generating methods. In a preferred embodiment, the forces are generated from the piezocrystals 705 in order to optimally provide a repeatable high-frequency pulse. The piezocrystals 705 are preferably charged to a high voltage. The piezocrystals 705 preferably shift from a resting position due to the high voltage. The high voltage of the piezocrystals 705 is preferably discharged. The piezocrystals 705 preferably create the forces as the piezocrystals 705 return to the resting position.

In step 1515, the forces created in step 1510 preferably create one or more responses in the accelerometers 305. The responses of the accelerometers 305 are preferably recorded as the response of the sensor module 105. The radio seismic recorder 120 preferably records the response of the sensor module 105.

In step 1520, the response of the sensor module 105 is preferably analyzed to find resonances and zeroes. In a preferred embodiment, the sensor module 105 does not have any resonances or zeroes in the frequency band of interest for seismic acquisition. If any resonances or zeroes are found in the frequency band of interest for seismic acquisition, they can be assumed to be caused by the ground itself or by the coupling to the ground of the sensor module 105. The frequency band of interest for seismic acquisition is roughly 1 Hz to 200 Hz. The analysis may be any conventional analysis used to estimate the transfer function of unknown systems. In a preferred embodiment, the analysis is an auto-regressive moving average (ARMA) model fit to the spectrum of the recorded data. After the transfer function has been estimated, the inverse of the transfer function is preferably used to greatly reduce the effects of non-ideal coupling.

Figure 16:
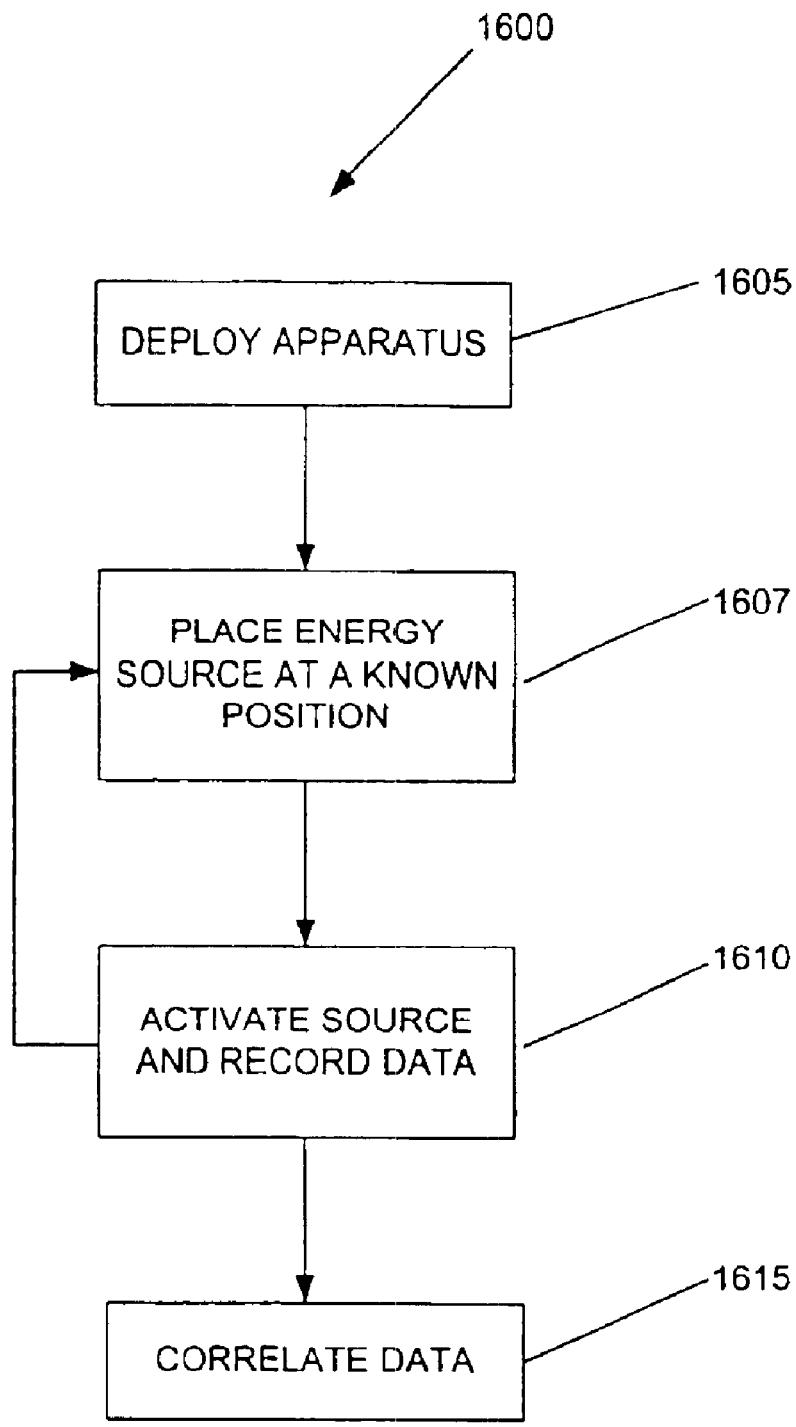
FIG. 16 is a block diagram of an embodiment of a method for determining the horizontal azimuth of the sensor module of FIG. 1.

Referring to FIG. 16, a preferred embodiment of a method 1600 for determining the horizontal azimuth of the sensor module 105 includes: (1) deploying the sensor module 105 in step 1605; (2) placing a seismic energy source at a known position in step 1607; (3) activating the energy source and recording one or more output signals in step 1610; repeating steps 1607 and 1610 such that at least two distinct source positions are used; and (4) correlating a range of data in step 1615.

In step 1605, one or more sensor modules 105 are preferably deployed completely beneath the Earth's surface. In several alternate embodiments, the sensor modules 105 may be deployed on or partially beneath the Earth's surface. The sensor modules 105 may be deployed using any number of conventional deployment methods. In a preferred embodiment, the sensor modules 105 are deployed in shallow, tight fitting holes in order to provide good coupling and noise reduction for a reasonable effort. In a preferred embodiment, in step 1605, the sensor modules 105 further derive a tilt angle for each sensor module 105 using the method 1200.

In step 1607, a seismic energy source is placed at a known position. The seismic energy source may be any type of conventional seismic energy sources, such as explosives or vibrator trucks.

In step 1610, the seismic energy source is preferably activated and the radio seismic recorder (RSR) 120 preferably records one or more output signals from the sensor modules 105. In an alternate embodiment, other seismic acquisition field boxes are used to record the output signals from the sensor modules 105. The activation of the seismic energy source preferably produces ground motion that will be detected by at least one of the sensor modules 105.

Steps 1607 and 1610 are repeated for at least two distinct seismic energy source locations. Determining the horizontal azimuth of the sensor modules 105 includes at least two distinct seismic source locations.

In an alternate embodiment, steps 1607 and 1610 are repeated a plurality of times to image the subsurface structure. The plurality of images produce a large set of data that may also be used to determine the horizontal azimuth of each sensor module 105.

In step 1615, an external data processor correlates the output signals from step 1610 to produce an estimate of the horizontal azimuth of the sensor modules 105. The external data processor may be a computer. The external data processor preferably finds the first breaks in the output signals that were recorded in step 1610. The first break in a seismic signal is the earliest time at which the source's energy becomes visible in the output signal. The external data processor preferably uses the plane of maximum vertical motion of first break data from step 1610, the known source location, and the known sensor module 105 location to estimate the horizontal azimuth of the sensor modules 105. The external data processor may estimate the horizontal azimuth of the sensor modules 105 using any number of conventional statistical methods. In a preferred embodiment, the external data processor estimates the horizontal azimuth of the sensor modules 105 using the maximum likelihood method in order to optimally provide a robust and accurate estimate. The plane of maximum vertical motion is the vertical plane that has the horizontal azimuth with the greatest seismic energy.

Figure 17:
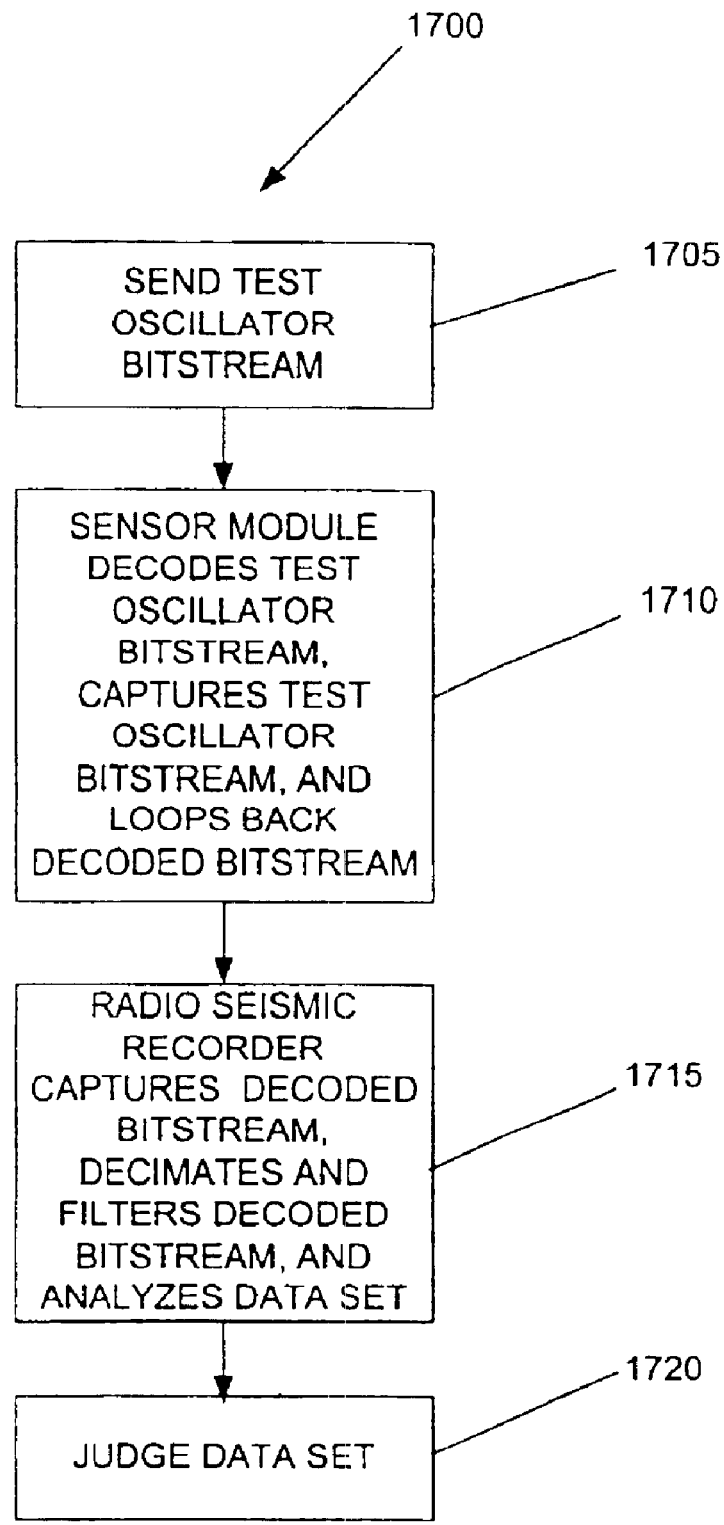
FIG. 17 is a block diagram of an embodiment of a method for determining the state-of-health of the system of FIG. 1.

Referring to FIG. 17, a preferred embodiment of a method 1700 for determining the state-of-health of the sensor module 105 and the radio seismic recorder 120 includes: (1) sending a test oscillator signal bitstream in step 1705; (2) decoding the test oscillator signal bitstream into a decoded bitstream, capturing the test oscillator signal bitstream, and looping back the decoded bitstream in step 1710; (3) capturing the decoded bitstream, decimating and filtering the decoded bitstream into a set of data in step 1715; and (4) judging the set of data in step 1720.

In step 1705, the RSR 120 preferably telemeters a test oscillator signal bitstream to the sensor module 105 through the communication interface 145. The test oscillator signal bitstream may be telemetered using any number of conventional telemetering methods. The test oscillator signal bitstream is preferably embedded in a digital command stream that is encoded. In a preferred embodiment, the encoding technique is manchester encoding in order to optimally provide data transfer and a good clock for the sensor module. The low frequency portion of the test oscillator signal bitstream telemetered in step 1705 may be, for example, sine wave data, impulsive data, sweep data, or other complex multi-frequency data. In a preferred embodiment, the low frequency portion of the test oscillator signal bitstream telemetered in step 1705 is sine wave data in order to provide a signal for which the distortion measurement is well defined.

In step 1710, the controller 220 decodes the digital command stream into a decoded bitstream, captures the test oscillator signal bitstream from the decoded bitstream, and loops-back the test oscillator signal bitstream to the RSR 120 via the communication interface 145. The controller 220 may decode the digital command stream using any number of conventional telemetry decoding techniques. In a preferred embodiment, the controller 220 decodes the digital command stream using a bit synchronous sampling technique in order to perform decoding with primarily digital circuitry and relatively simple analog circuitry. The controller 220 preferably captures the test oscillator signal bitstream by extracting it from the digital command stream that contains other data as well. The controller 220 preferably loops back the test oscillator signal bitstream by transmitting it to the RSR 120 in place of the regular seismic data bitstream. The controller 220 preferably encodes the test oscillator signal bitstream for transmission back to the RSR 120 using manchester encoding. The sensor module 105 preferably has a plurality of accelerometers 305, and the controller 220 preferably replaces the data from each accelerometer 305 with a copy of the test oscillator signal bitstream.

In step 1715, the RSR 120 preferably decodes the returned test oscillator signal bitstream, captures the returned test oscillator signal bitstream, decimates and filters the captured test oscillator signal bitstream into a set of data, and analyzes the set of data. The RSR 120 may decode the returned test oscillator signal bitstream using any number of conventional telemetry decoding techniques. In a preferred embodiment, the RSR 120 decodes the returned test oscillator signal bitstream using a bit synchronous sampling technique in order to perform decoding with primarily digital circuitry and relatively simple analog circuitry. The RSR 120 preferably captures the returned test oscillator signal bitstream by extracting it from the returned test oscillator signal bitstream that may contain other data as well. The RSR 120 may decimate and filter the returned test oscillator signal bitstream into a set of data using any number of conventional decimating and filtering methods. The analysis of the set of data in step 1715 may be, for example, time-domain sample sequence analysis or frequency domain analysis. Time-domain sample sequence analysis may be, for example, offset, peak (maximum and/or minimum), or root-mean-square. Frequency domain analysis may be, for example, amplitude spectra, phase spectra, or total harmonic distortion. In a preferred embodiment, the analysis of the set of data in step 1715 is a time domain channel-to-channel matching test and a total harmonic distortion measurement in order to optimally provide a thorough test of data path reliability.

In step 1720, the RSR 120 preferably judges whether the set of data is acceptable or not. The RSR 120 may judge the set of data using any number of conventional judging methods. The RSR 120 preferably judges the set of data to be unacceptable if for any specific time within the data set the data channels are not equal. The data channels should all be equal because the sensor module 105 was supposed to put the test oscillator signal bitstream on all channels. The RSR 120 also preferably judges the set of data to be unacceptable if the total harmonic distortion exceeds a threshold. An unacceptable set of data indicates a malfunction of the sensor module 105, the communication interface 145, or the radio seismic recorder 120.

Figure 18:
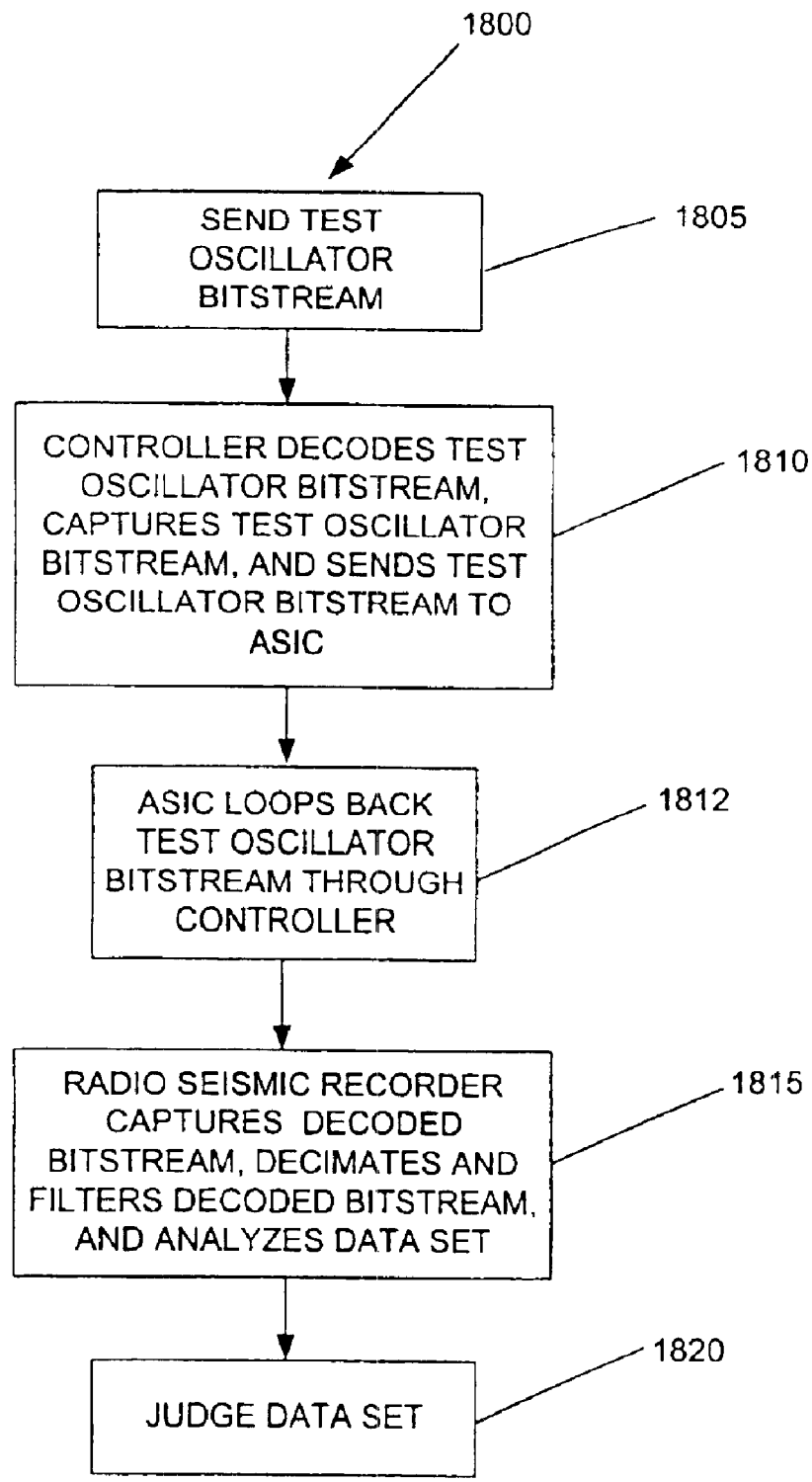
FIG. 18 is a block diagram of an embodiment of a method for determining the state-of-health of the accelerometers of FIG. 4 of the system of FIG. 1.

Referring to FIG. 18, a preferred embodiment of a method 1800 for determining the state-of-health of the accelerometers 305 includes: (1) sending a test oscillator signal bitstream in step 1805; (2) decoding the test oscillator bitstream, capturing the test oscillator signal bitstream, and sending the test oscillator signal bitstream to one or more ASICs 410 in step 1810; (3) looping back the decoded bitstream in step 1812; (4) capturing the decoded bitstream, decimating and filtering the decoded bitstream into a set of data and analyzing the set of data in step 1815; and (5) judging the set of data in step 1820.

In step 1805, the RSR 120 preferably telemeters a test oscillator signal bitstream to the sensor module 105 via the communication interface 145. The test oscillator signal bitstream may be telemetered using any number of conventional telemetering methods. The test oscillator signal bitstream is preferably embedded in a digital command stream that is encoded. In a preferred embodiment, the encoding technique is manchester encoding in order to provide data transfer and a good clock for the sensor module 105. The low frequency portion of the test oscillator signal bitstream telemetered in step 1805 may be, for example, sine wave data, impulsive data, sweep data, or other complex multi-frequency data.

In step 1810, the controller 220 preferably decodes the digital command stream into a decoded bitstream, captures the test oscillator signal bitstream from the decoded bitstream, and sends the received test oscillator signal bitstream to one or more ASICs 410. The controller 220 may decode the digital command stream using any conventional telemetry decoding techniques. In a preferred embodiment, the controller 220 decodes the digital command stream using a bit synchronous sampling technique in order to perform decoding with primarily digital circuitry and relatively simple analog circuitry. The controller 220 preferably captures the test oscillator signal bitstream by extracting it from the digital command stream, that contains other data as well. The controller 220 preferably transfers the test oscillator signal bitstream to the ASICs 410 of the accelerometers 305.

In step 1812, the ASICs 410 preferably loop back the test oscillator signal bitstream. The test oscillator signal bitstream becomes an input to the ASICs 410. The ASICs 410 can loop back the test oscillator signal bitstream using any conventional loop back technique. The ASICs 410 preferably create an ASIC bitstream which at low frequencies will be substantially the opposite of the low frequency portion of the test oscillator signal bitstream. Low frequencies are those substantially below the Nyquist frequency of the test oscillator signal bitstream. In a preferred embodiment, low frequencies are frequencies below approximately 500 hertz in order to provide testing at the frequencies of interest for seismic recording. The ASICs 410 preferably send the ASIC bitstream to the controller 220 using the communication interface 245b. The controller 220 preferably transmits the ASIC bitstream to the RSR 120. The controller 220 preferably encodes the ASIC bitstream for transmission back to the RSR 120 using manchester encoding.

In several alternate embodiments, the ASICs 410 may create an ASIC bitstream which is exactly identical to the test oscillator signal bitstream or an ASIC bitstream which is a delayed copy of the test oscillator signal bitstream.

In step 1815, the RSR 120 preferably decodes the returned ASIC bitstream, captures the returned ASIC bitstream, decimates and filters the ASIC bitstream into a set of data, and analyzes the set of data. The RSR 120 may decode the returned ASIC bitstream using any conventional telemetry decoding techniques. In a preferred embodiment, the RSR 120 decodes the ASIC bitstream using a bit synchronous sampling technique in order to perform decoding with primarily digital circuitry and relatively simple analog circuitry. The RSR 120 preferably captures the ASIC bitstream by extracting the ASIC bitstream from the returned ASIC bitstream that contains other data as well. The RSR 120 may decimate and filter the ASIC bitstream into a set of data using any number of conventional decimating and filtering methods. The analysis of the set of data in step 1815 may be, for example, time-domain sample sequence analysis or frequency domain analysis. Time-domain sample sequence analysis may be, for example, offset, peak (maximum and/or minimum), or root-mean-square. Frequency domain analysis may be, for example, amplitude spectra, phase spectra, or total harmonic distortion. In a preferred embodiment, the analysis of the set of data in step 1815 is a total harmonic distortion measurement and a signal-to-noise measurement in order to optimally provide a thorough test of signal quality.

In step 1820, the RSR 120 preferably judges whether the set of data is acceptable or not. The RSR 120 may judge the set of data using any number of conventional judging methods. The RSR 120 preferably judges the set of data to be unacceptable if the total harmonic distortion exceeds a threshold. In an alternate embodiment, the RSR 120 may judge the set of data to be unacceptable if the signal to noise ratio falls below a different threshold. An unacceptable set of data indicates a malfunction of the communication interface 145 or one or more components of the sensor module 105.

Figure 19:
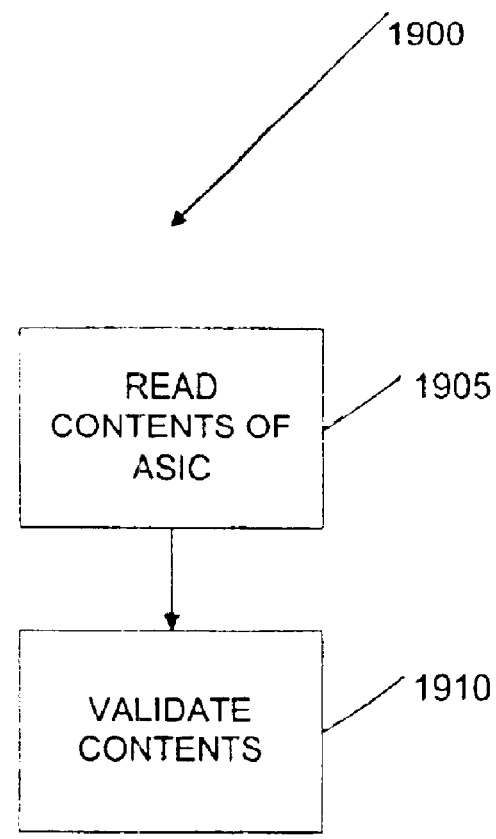
FIG. 19 is a block diagram of an alternate embodiment of a method for determining the state-of-health of the accelerometers of FIG. 4 of the system of FIG. 1.

Referring to FIG. 19, an embodiment of a method 1900 for determining the state-of-health of the accelerometers 305 includes: (1) reading the contents of the ASIC 410 in step 1905; and (2) validating the contents in step 1910. The contents of the ASIC 410 preferably include one or more configurable contents. The configurable contents of the ASIC 410 preferably includes a cyclic redundancy code (CRC) word.

In step 1905, the controller 220 preferably reads the contents of the ASIC 410 for each corresponding accelerometer 305 via the communication interface 245b. The communication interface 245b preferably includes a serial bus through which the internal memory of the ASIC 410 may be read and written. The controller 220 preferably transfers the contents of the ASIC 410 to the RSR 120 via the communication interface 145.

In step 1910, the RSR 120 preferably validates the contents of the ASIC 410 for each corresponding accelerometer 305 from step 1905. In a preferred embodiment, the RSR 120 uses a CRC algorithm to validate the contents of the ASIC 410 for each corresponding accelerometer 305 in order to optimally provide verification of the integrity of the contents of the ASIC 410. A miscomparison of the contents of the ASIC 410 or an error indicated by checking the CRC word of the corresponding accelerometer 305 by the RSR 120 may indicate a malfunction. The method 1900 may be performed on a single accelerometer 305 or on a plurality of accelerometers 305.

A miscomparison of the contents of the ASIC 410 or an error indicated by checking the CRC word of the corresponding accelerometer 305 by the RSR 120 may also indicate an error in configuration of the corresponding accelerometer 305.

Figure 20:
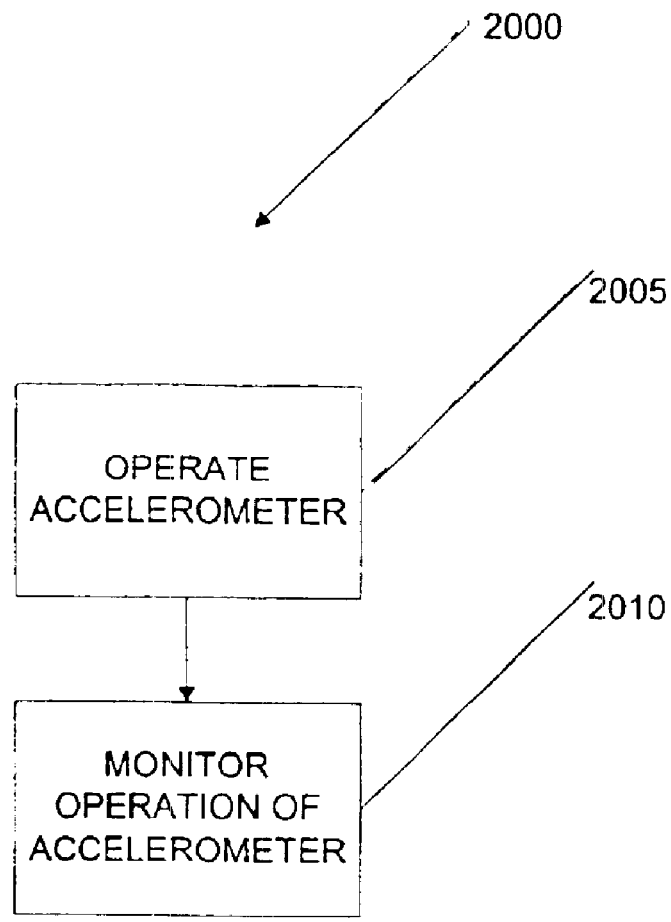
FIG. 20 is a block diagram of an alternate embodiment of a method for determining the state-of-health of the accelerometers of FIG. 4 of the system of FIG. 1.

Referring to FIG. 20, another embodiment of a method 2000 for determining the state-of-health of the accelerometers 305 includes: (1) operating the first accelerometer 305a in step 2005; and (2) monitoring the operation of the first accelerometer 305a in step 2010.

In step 2005, the first accelerometer 305a may be operated in any of the accelerometer's available operating modes. The first accelerometer 305a preferably generates output signals containing information pertaining to the stability of the first accelerometer 305a during operation. The stability of the accelerometers 305 is preferably provided as disclosed in the following: copending U.S. patent application Ser. No. 09/936,630, filed on Sep. 14, 2001, the disclosure of which is incorporated herein by reference.

In step 2010, the RSR 120 preferably monitors the operation of the first accelerometer 305a via the communication interface 145. The RSR 120 preferably monitors the operation of the first accelerometer 305a by capturing and evaluating the stability related signals generated by the first accelerometer 305a in step 2005. The RSR 120 may, for example, monitor the ability of the first accelerometer 305a to become stable within a specified period of time or may monitor one or more status signals and responses of the ASIC 410 of the first accelerometer 305a for continuing stability. In a preferred embodiment, the RSR 120 monitors the status signal generated by the ASIC 410 of the first accelerometer 305a in order to optimally provide verification of the stability of the first accelerometer 305a. The status signal generated by the ASIC 410 of the first accelerometer 305a may be a signal that indicates the data is valid. An indication of instability of the first accelerometer 305a monitored by the RSR 120 preferably indicates a malfunction of the first accelerometer 305a or an excessively noisy external environment.

In an alternate embodiment, the second accelerometer 305b is substituted for the first accelerometer 305a. In another alternate embodiment, the third accelerometer 305c is substituted for the first accelerometer 305a In another alternate embodiment, one or more accelerometers 305 may be substituted for the first accelerometer 305a.

Figure 21:
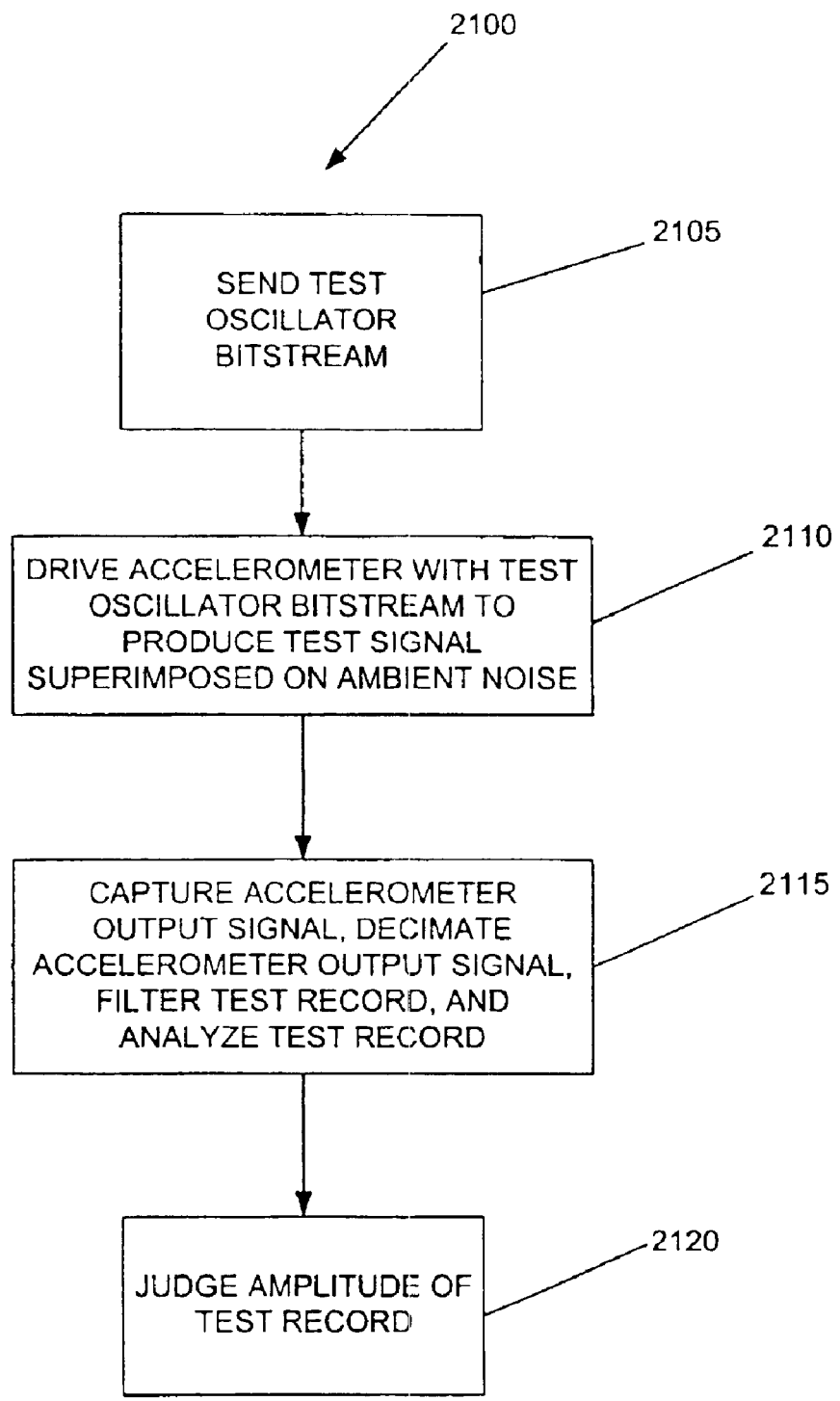
FIG. 21 is a block diagram of an alternate embodiment of a method for determining the state-of-health of the accelerometers of FIG. 4 of the system of FIG. 1.

Referring to FIG. 21, another embodiment of a method 2100 for determining the state-of-health of the accelerometers 305 includes: (1) sending a test oscillator signal bitstream in step 2105; (2) superimposing the test oscillator signal bitstream in step 2110; (3) capturing a superimposed test oscillator signal bitstream, decimating the superimposed test oscillator signal bitstream into a test record, filtering the test record and analyzing the test record in step 2115; and (4) judging a magnitude of amplitude of the test record in step 2120.

In step 2105, the RSR 120 preferably telemeters a test oscillator signal bitstream to the first accelerometer 305a of the sensor module 105 via the communication interface 145. The test oscillator signal bitstream may be telemetered using any number of conventional telemetering methods. In a preferred embodiment, the test oscillator signal bitstream is telemetered with sensor module 105 command bits interleaved in order to reduce sensor module 105 buffering requirements. The test oscillator signal bitstream telemetered may be, for example, sine wave data, impulse data, swept data, or other complex multi-frequency data. In a preferred embodiment, the test oscillator signal bitstream telemetered is sine wave data in order to optimally provide simplified analysis of signal amplitude.

In step 2110, the first accelerometer 305a preferably receives the test oscillator signal bitstream and the test oscillator signal bitstream drives the first accelerometer 305a. Driving the first accelerometer 305a by the test oscillator signal bitstream preferably produces a superimposed test oscillator signal bitstream. The driving of the accelerometers 305 using a test signal bitstream is preferably provided as disclosed in the following: U.S. Pat. No. 6,023,960, the disclosure of which is incorporated herein by reference. The superimposed test oscillator signal bitstream is created from the test oscillator signal bitstream being superimposed upon the ambient signal and noise acceleration of the first accelerometer 305a.

In step 2115, the RSR 120 preferably captures the superimposed test oscillator signal bitstream from step 2110 via the communication interface 145, decimates the superimposed test oscillator signal bitstream into a test record, filters the test record, and analyzes the test record. The analysis of the test record in step 2115 may be performed using any number of conventional methods for analyzing signal amplitude. The analysis of the test record in step 2115 is preferably performed by calculating the difference between the magnitude of the frequency of interest in the test record and the magnitude of the same frequency in a reference test record acquired from the first accelerometer 305a using the digital loopback mode outlined in step 1710 of the method 1700 in FIG. 17.

In step 2120, the magnitude of the test record is judged to be acceptable or not by, for example, the controller 110 or another component of the system 100. The magnitude of the test record may be judged using any number of conventional judging methods. In a preferred embodiment, the magnitude of the test record is judged by comparing the difference between the magnitude differences calculated in step 2115 and a mean magnitude difference calculated from the magnitude differences of other accelerometers 305, to a specified magnitude difference limit in order to optimally provide an indication of acceptance or failure of the first accelerometer 305a response. The method 2100 is preferably not performed under extreme high ambient signal and noise conditions.

In an alternate embodiment, the reference test record of step 2115 is not used. The magnitude of the test record is judged by comparing the difference between the magnitude of the frequency of interest in the test record and a mean magnitude of the frequency of interest in test records from other accelerometers 305 to a specified magnitude difference limit.

In an alternate embodiment, the second accelerometer 305b is substituted for the first accelerometer 305a. In another alternate embodiment, the third accelerometer 305c is substituted for the first accelerometer 305a In another alternate embodiment, one or more accelerometers 305 may be substituted for the first accelerometer 305a.

Figure 22:
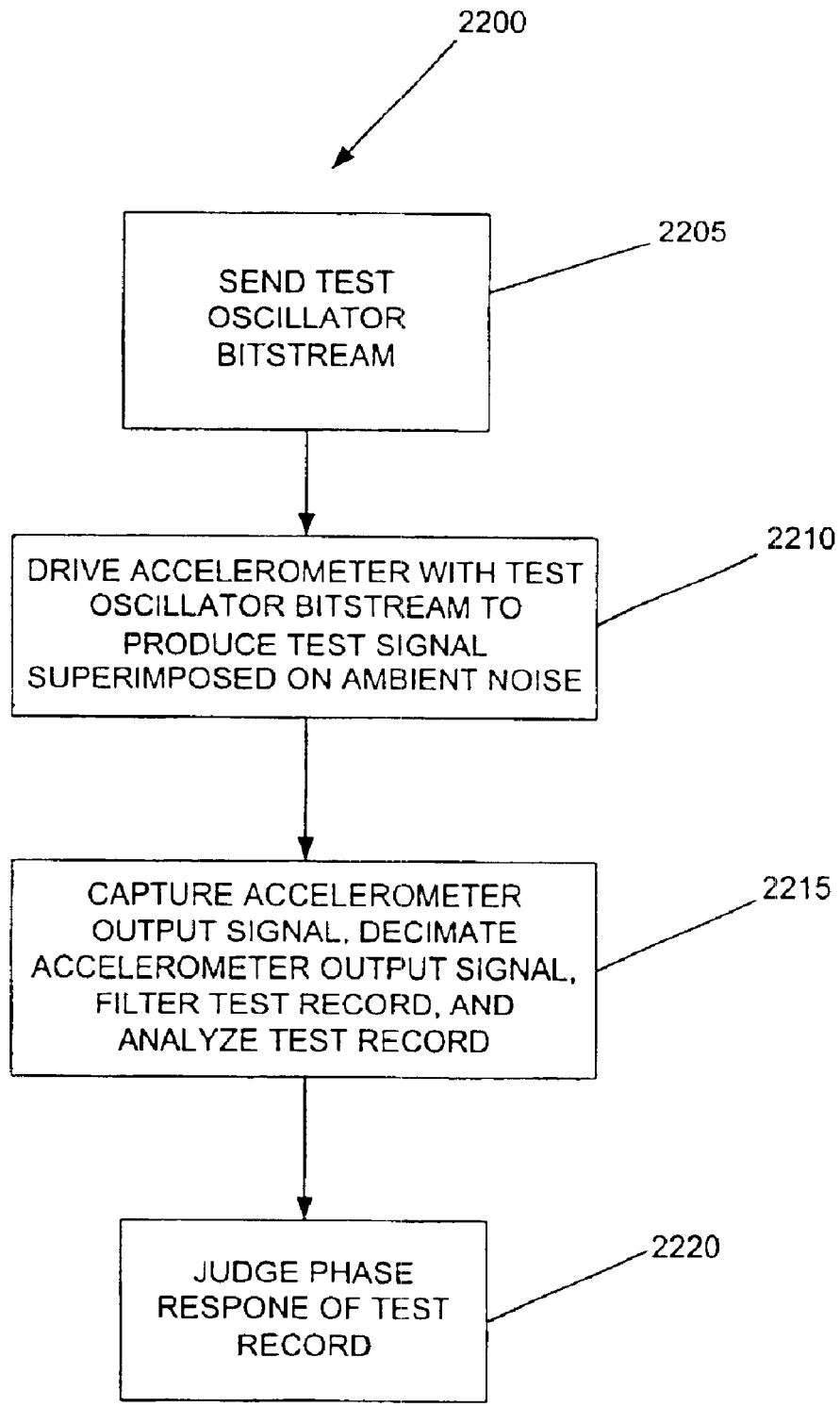
FIG. 22 is a block diagram of an alternate embodiment of a method for determining the state-of-health of the accelerometers of FIG. 4 of the system of FIG. 1.

Referring to FIG. 22, another embodiment of a method 2200 for determining the state-of-health of the accelerometers 305 includes: (1) sending a test oscillator signal bitstream in step 2205; (2) superimposing the test oscillator signal bitstream in step 2210; (3) capturing the superimposed test oscillator signal bitstream, decimating the superimposed test oscillator signal bitstream into a test record, filtering the test record and analyzing the test record in step 2215; and (4) judging a phase response of the test record in step 2220.

In step 2205, the RSR 120 preferably telemeters a test oscillator signal bitstream to the first accelerometer 305a of the sensor module 105 via the communication interface 145. The test oscillator signal bitstream may be telemetered using any number of conventional telemetering methods. In a preferred embodiment, the test oscillator signal bitstream is telemetered with sensor module 105 command bits interleaved in order to reduce sensor module 205 buffering requirements. The test oscillator signal bitstream telemetered may be, for example, sine wave data, impulse data, swept data, or other complex multi-frequency data. In a preferred embodiment, the test oscillator signal bitstream telemetered is sine wave data in order to optimally provide simplified analysis of phase response.

In step 2210, the first accelerometer 305a receives the test oscillator signal bitstream and the test oscillator signal bitstream is used to drive the first accelerometer 305a. Driving the first accelerometer 305a by the test oscillator signal bitstream preferably produces a superimposed test oscillator signal bitstream. The driving of the accelerometers 305 using a test signal bitstream is preferably provided as disclosed in the following: U.S. Pat. No. 6,023,960, the disclosure of which is incorporated herein by reference. The superimposed test oscillator signal bitstream is created from the test oscillator signal bitstream being superimposed upon the ambient signal and noise acceleration of the first accelerometer 305a.

In step 2215, the RSR 120 preferably captures the superimposed test oscillator signal bitstream from step 2210 via the communication interface 145, decimates the superimposed test oscillator signal bitstream into a test record, filters the test record, and analyzes the test record. The analysis of the test record may be performed using any number of conventional methods for analyzing phase response. The analysis of the test record is preferably performed by calculating the difference between the phase of the frequency of interest in the test record and the phase of the same frequency in a reference test record acquired from the first accelerometer 305a using the digital loopback mode outlined in step 1710 of the method 1700 in FIG. 17.

In step 2220, the phase response of the test record is judged to be acceptable or not by, for example, the controller 110 or another component of the system 100. The phase response of the test record may be judged using any number of conventional judging methods. In a preferred embodiment, the phase response of the test record is judged by comparing the difference between the phase difference calculated in step 2215 and a mean phase difference calculated from the phase differences of other accelerometers 305, to a specified phase difference limit in order to optimally provide an indication of acceptance or failure of the first accelerometer 305a phase response. The method 2200 is preferably not performed under extreme high ambient signal and noise conditions.

In an alternate embodiment, the reference test record in step 2215 is not used. The phase response of the test record is judged by comparing the difference between the phase of the frequency of interest in the test record to a mean phase of the same frequency in test records from other accelerometers 305 to a specified phase limit.

In an alternate embodiment, the second accelerometer 305b is substituted for the first accelerometer 305a. In another alternate embodiment, the third accelerometer 305c is substituted for the first accelerometer 305a. In another alternate embodiment, one or more accelerometers 305 are substituted for the first accelerometer 305a.

Figure 23:
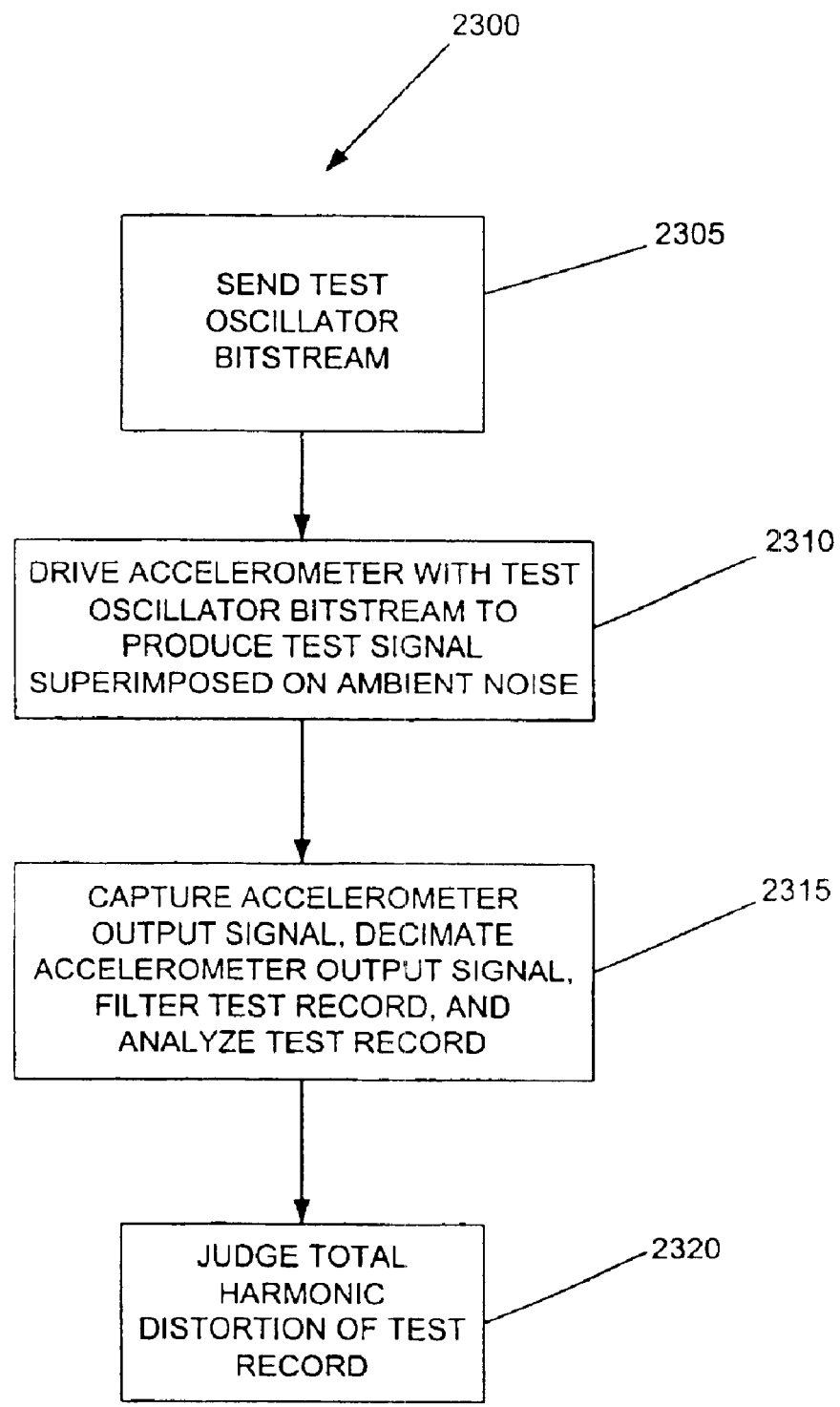
FIG. 23 is a block diagram of an alternate embodiment of a method for determining the state-of-health of the accelerometers of FIG. 4 of the system of FIG. 1.

Referring to FIG. 23, another embodiment of a method 2300 for determining the state-of-health of the accelerometers 305 includes: (1) sending a test oscillator signal bitstream in step 2305; (2) superimposing the test oscillator signal bitstream in step 2310; (3) capturing the superimposed test oscillator signal bitstream, decimating the superimposed test oscillator signal bitstream into a test record, filtering the test record and analyzing the test record in step 2315; and (4) judging a total harmonic distortion of the test record in step 2320.

In step 2305, the RSR 120 preferably telemeters a test oscillator signal bitstream to the first accelerometer 305a of the sensor module 105 via the communication interface 145. The test oscillator signal bitstream may be telemetered using any number of conventional telemetering methods. In a preferred embodiment, the test oscillator signal bitstream is telemetered with sensor module 105 command bits interleaved in order to reduce sensor module 105 buffering requirements. The test oscillator signal bitstream telemetered may be, for example, sine wave data, impulse data, swept data, or other complex multi-frequency data. In a preferred embodiment, the test oscillator signal bitstream telemetered is sine wave data in order to optimally provide simplified analysis of harmonic distortion.

In step 2310, the first accelerometer 305a preferably receives the test oscillator signal bitstream and the test oscillator signal bitstream is used to drive the first accelerometer 305a. Driving the first accelerometer 305a by the test oscillator signal bitstream produces a superimposed test oscillator signal bitstream. The driving of the accelerometers 305 using a test signal bitstream is preferably provided as disclosed in the following: U.S. Pat. No. 6,023,960, the disclosure of which is incorporated herein by reference. The superimposed test oscillator signal bitstream is created from the test oscillator signal bitstream being superimposed upon the ambient signal and noise acceleration of the first accelerometer 305a.

In step 2315, the RSR 120 preferably captures the superimposed test oscillator signal bitstream via the communication interface 145, decimates the superimposed test oscillator signal bitstream into a test record, filters the test record, and analyzes the test record. The analysis of the test record may be performed using any number of conventional methods for analyzing harmonic distortion. The analysis of the test record is preferably performed by comparing the power contained in the test record at the fundamental frequency provided by the test oscillator signal to the power contained in the test record at the harmonics of the fundamental frequency.

In step 2320, the RSR 120 preferably judges whether the test record is acceptable or not. The RSR 120 may judge a total harmonic distortion of the test record using any number of conventional judging methods. In a preferred embodiment, the RSR 120 judges the total harmonic distortion of the test record by comparing the difference between the test record's fundamental and harmonic power to a specified harmonic distortion limit in order to optimally provide an indication of acceptance or failure of the first accelerometer 305a response. The method 2300 is preferably not performed under extreme high ambient signal and noise conditions.

In an alternate embodiment, the second accelerometer 305b is substituted for the first accelerometer 305a. In another alternate embodiment, the third accelerometer 305c is substituted for the first accelerometer 305a. In another alternate embodiment, one or more accelerometers 305 may be substituted for the first accelerometer 305a.

Figure 24:
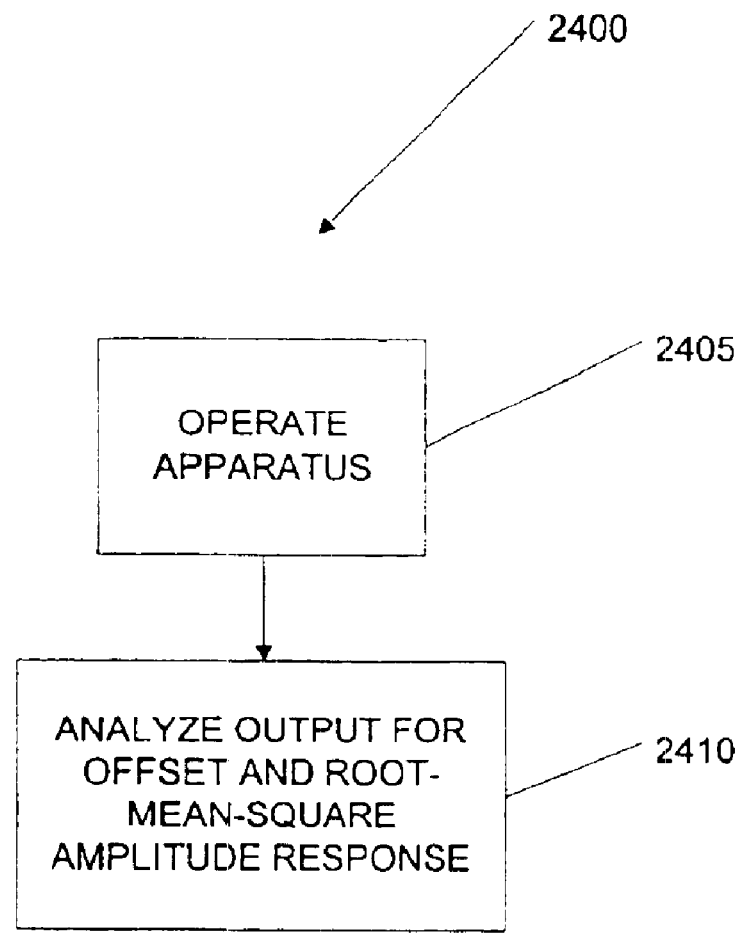
FIG. 24 is a block diagram of an alternate embodiment of a method for determining the state-of-health of the accelerometers of FIG. 4 of the system of FIG. 1.

Referring to FIG. 24, another embodiment of a method 2400 for determining the state-of-health of the accelerometers 305 includes: (1) operating the accelerometers 305 in step 2405; and (2) analyzing the output for offset and root-mean-square amplitude response step 2410.

In step 2405, the first accelerometer 305a of the sensor module 105 is preferably operated for a period of time. The first accelerometer 305a may be operated using any number of conventional operating methods. The first accelerometer 305a is preferably operated for sensing seismic data. The period of time may range, for example, from about 0.5 to 99 second or more. In a preferred embodiment, the period of time is about 2.048 seconds in order to provide ample data to evaluate sensor noise.

In step 2410, the RSR 120 preferably captures an output signal from the first accelerometer 305a via the communication interface 145. The RSR 120 may capture the output signal using any number of conventional reception methods. In a preferred embodiment, in step 2410, the RSR 120 further calculates the root mean square (RMS) amplitude of the received output signal and the offset of the received output signal. The RSR 120 may calculate the RMS amplitude and offset using any number of conventional calculation methods. In a preferred embodiment, the RSR 120 performs the calculation using the controller 610 in order to optimally provide accuracy and flexibility. In a preferred embodiment, in step 2410, the RSR 120 further judges whether the output signal is acceptable or not against acceptance criteria. The RSR 120 may judge the output signal using any number of conventional judging methods. In a preferred embodiment, the RSR 120 judges the output signal using the calculated RMS amplitude and offset values in order to optimally provide an indication of the acceptance or failure of the first accelerometer 305a output signal. The acceptance criteria may be, for example, RMS amplitude greater than a minimum limit and less than a maximum limit, or offset less than a specified limit. In a preferred embodiment, the acceptance criteria is RMS amplitude less than about −72 dBg in order to optimally provide verification of low sensor noise. The failure of the output signal to meet the acceptance criteria may indicate an internal problem with the first accelerometer 305a or an excessively noisy external environment.

In an alternate embodiment, the second accelerometer 305b is substituted 23 for the first accelerometer 305a. In another alternate embodiment, the third accelerometer 305c is substituted for the first accelerometer 305a. In another alternate embodiment, one or more accelerometers 305 may be substituted for the first accelerometer 305a.

Figure 25:
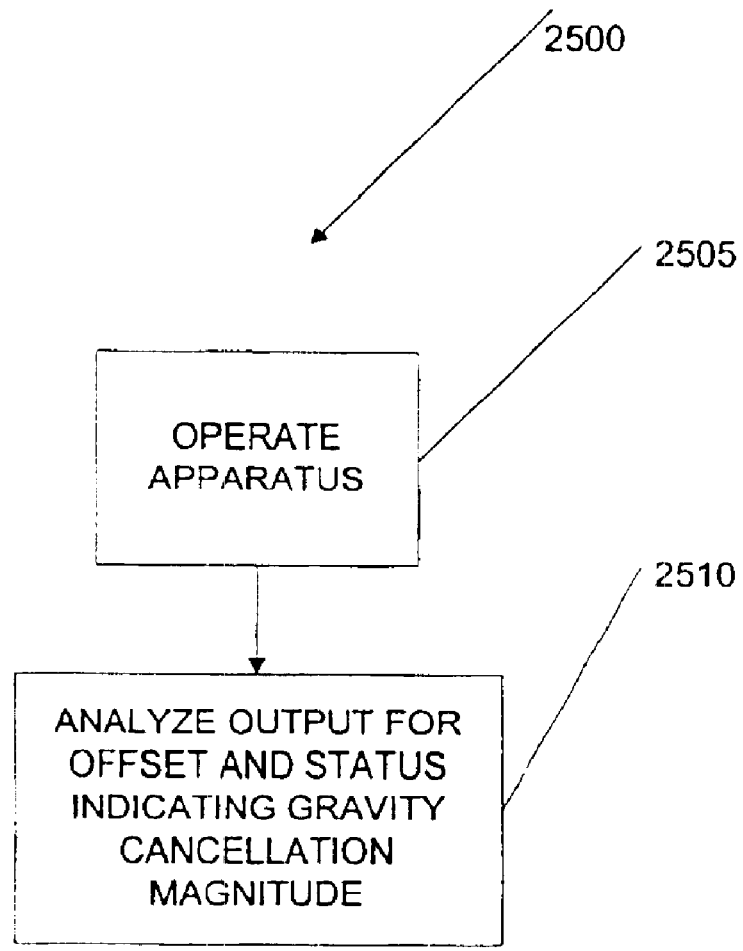
FIG. 25 is a block diagram of an alternate embodiment of a method for determining the state-of-health of the accelerometers of FIG. 4 of the system of FIG. 1.

Referring to FIG. 25, another embodiment of a method 2500 for determining the state-of-health of the accelerometers 305 includes: (1) operating the accelerometers 305 in step 2505; and (2) analyzing an output signal for offset and status indicating gravity cancellation magnitude in step 2510. The calculation of gravity cancellation magnitude of the accelerometers 305 is preferably provided as disclosed in the following: copending U.S. patent application Ser. No. 09/936,630, filed on Sep. 14, 2001, the disclosure of which is incorporated herein by reference.

In step 2505, the first accelerometer 305a of the sensor module 105 is preferably operated. The first accelerometer 305a may be operated using any number of conventional operating methods. The first accelerometer 305a is preferably operated for sensing seismic data.

In step 2510, the RSR 120 preferably captures an output signal from the first accelerometer 305a via the communication interface 145. The RSR 120 may capture the output signal using any number of conventional reception methods. The output signal preferably includes an offset caused by imperfect cancellation of gravity by the first accelerometer 305a and a status indicating gravity cancellation magnitude. In a preferred embodiment, in step 2510, the RSR 120 further calculates the magnitude of the gravity to which the first accelerometer 305a is exposed. The RSR 120 preferably calculates the magnitude of the gravity to which the first accelerometer 305a is exposed using the gravity cancellation magnitude provided by the first accelerometer 305a and the offset calculated from the seismic data. In a preferred embodiment, in step 2510, the RSR 120 further calculates an error between the calculated gravity and the status indicating gravity cancellation magnitude. The RSR 120 may calculate the error using any number of conventional calculation methods. An error of greater than about 5% may indicate the first accelerometer 305a has changed tilt or that the first accelerometer 305a did not initialize properly.

In an alternate embodiment, the second accelerometer 305b is substituted for the first accelerometer 305a. In another alternate embodiment, the third accelerometer 305c is substituted for the first accelerometer 305a. In another alternate embodiment, one or more accelerometers 305 may be substituted for the first accelerometer 305a.

Figure 26:
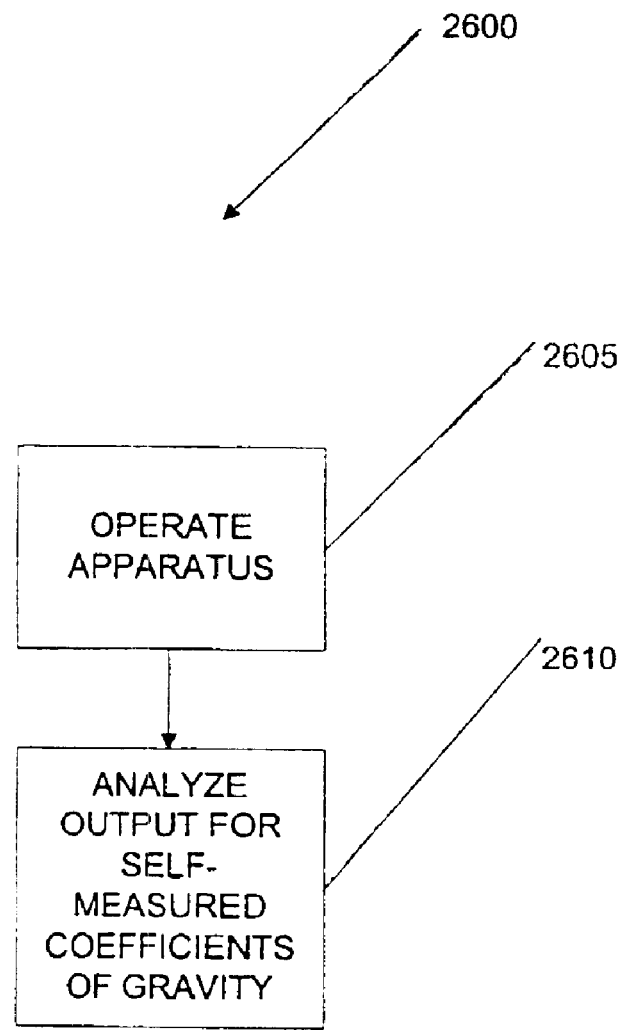
FIG. 26 is a block diagram of an embodiment of a method for determining the state-of-health of the sensor assembly of FIG. 2 of the system of FIG. 1.

Referring to FIG. 26, a preferred embodiment of a method 2600 for determining the state-of-health of the sensor assembly 210 includes: (1) operating the sensor module 105 in step 2605; and (2) analyzing one or more output signals for self-measured coefficients of gravity in step 2610.

In step 2605, the accelerometers 305 of the sensor module 105 are preferably operated. The accelerometers 305 are preferably operated such that they calculate the magnitude of the gravity field in which they are operating. The calculation of the magnitude of the gravity field of the accelerometers 305 is preferably provided as disclosed in the following: copending U.S. patent application Ser. No. 09/936,630, filed on Sep. 14, 2001, the disclosure of which is incorporated herein by reference.

In step 2610, the RSR 120 preferably collects one or more output signals from the accelerometers 305 via the communication interface 145. There are preferably three output signals, one from each accelerometer 305. The RSR 120 may collect the three output signals using any number of conventional collection methods. In a preferred embodiment, the RSR 120 collects the three output signals using a balanced twisted wire pair in order to optimally provide reliable data transfer. In a preferred embodiment, in step 2610, the RSR 120 further analyzes the three output signals. The three output signals preferably include one or more self-measured coefficients of gravity for each of the accelerometers 305. In a preferred embodiment, there are three self-measured coefficients of gravity, one for each accelerometer 305. In a preferred embodiment, in step 2610, the RSR 120 further calculates a vector sum of the three coefficients of gravity. In a preferred embodiment, in step 2610, the RSR 120 further compares the vector sum of the three coefficients of gravity to +1 g-force and calculates an error. The error may range, for example, from about 0 to 0.2 g. In a preferred embodiment, the error ranges from about 0 to 0.05 g in order to optimally provide verification of proper accelerometer 305 operation. An error outside the indicated range preferably indicates that the sensor assembly 210 has become unstable or malfunctioned.

Figure 27:
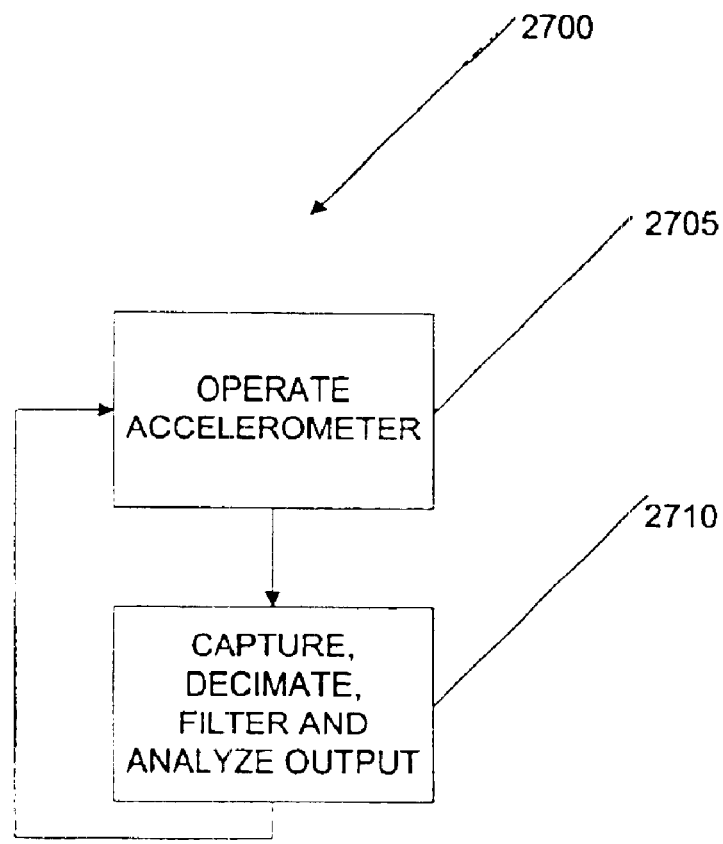
FIG. 27 is a block diagram of an alternate embodiment of a method for determining the state-of-health of the sensor assembly of FIG. 2 of the system of FIG. 1.

Referring to FIG. 27, another embodiment of a method 2700 for determining the state-of-health of the sensor assembly 210 includes: (1) operating the accelerometers 305 of the sensor assembly 210 in step 2705; and (2) capturing an output signal, decimating the output signal to a data record, filtering the data record and analyzing the data record in step 2710.

In step 2705, all accelerometers 305 are preferably operated. In a preferred embodiment, the first accelerometer 305a is operated in the manner normally used to acquire seismic data. The operation of the first accelerometer 305a in the manner normally used to acquire seismic data preferably provides an opportunity for crossfeed. In a preferred embodiment, in step 2705, the RSR 120 further drives the second accelerometer 305b and the third accelerometer 305c at a reference frequency using a test signal bitstream. The reference frequency may be any conventional frequency desired to test for crossfeed into the first accelerometer 305a. The driving of the accelerometers 305 using a test signal bitstream is preferably provided as disclosed in the following: U.S. Pat. No. 6,023,960, the disclosure of which is incorporated herein by reference.

In step 2710, the RSR 120 preferably captures one or more output signals from the accelerometers 305 via the communication interface 145, decimates the output signal to a data record, filters the data record, and analyzes the data record. The analysis of the data record in step 2710 may be any conventional analysis appropriate to detect crossfeed. In a preferred embodiment, the data record is analyzed by comparing the amplitude of each accelerometer's 305 output at the reference frequency when driven at the reference frequency to the amplitude of the accelerometer's 305 output at the reference frequency when configured for seismic data acquisition in order to optimally provide detection of crossfeed in the accelerometers 305. In a preferred embodiment, the RSR 120 further judges the signal amplitude of the first accelerometer 305a at the reference frequency due to crossfeed to be less than a threshold. The threshold may range, for example, from about −40 to −52 dB. In a preferred embodiment, the threshold is less than about −52 dB.

In a preferred embodiment, method 2700 further rotates through each of the accelerometers 305. The operation of the accelerometers 305 is preferably rotated so that each of the accelerometers 305 is operated in the manner normally used to acquire seismic data, while the remaining accelerometers 305 are driven at a reference frequency. In an exemplary embodiment, the first rotation preferably has the first accelerometer 305a operating in the manner normally used to acquire seismic data, and the second and third accelerometers 305b and 305c are driven at a reference frequency. The second rotation preferably has the second accelerometer 305b operating in the manner normally used to acquire seismic data, and the first and third accelerometers 305a and 305c are preferably driven at the reference frequency. The third rotation preferably has the third accelerometer 305c operating in the manner normally used to acquire seismic data, and the first and second accelerometers 305a and 305b are preferably driven at the reference frequency. The rotation of the operation of the accelerometers 305 may be done in any order. All accelerometers 305 preferably meet the threshold to validate the operation of the sensor assembly 210 as described in step 2710. The method 2700 is preferably not performed under extreme high ambient signal and noise conditions.

Figure 28:
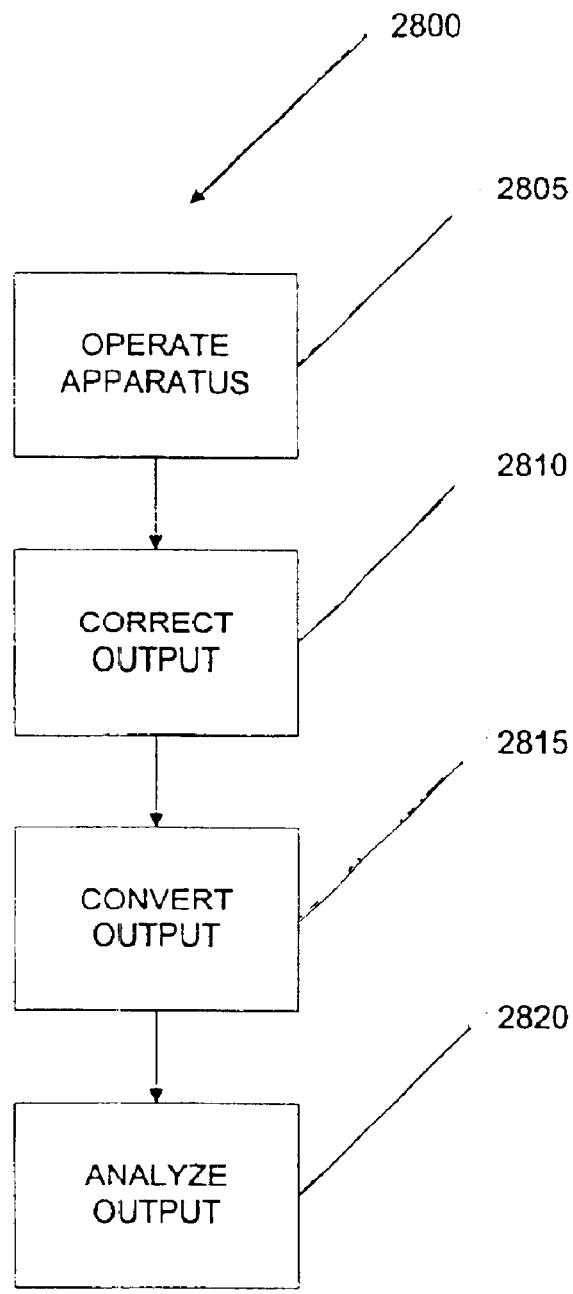
FIG. 28 is a block diagram of an alternate embodiment of a method for determining the state-of-health of the sensor assembly of FIG. 2 of the system of FIG. 1.

Referring to FIG. 28, another embodiment of a method 2800 for determining the state-of-health of the sensor assembly 210 includes: (1) operating the sensor assembly 210 in step 2805; (2) correcting an output signal in step 2810; (3) converting the output signal in step 2815; and (4) analyzing the output signal in step 2820.

In step 2805, the sensor assembly 210 is preferably operated for a period of time. The period of time may be any period of time desired. In a preferred embodiment, the period of time ranges from about 0.5 to 50 seconds.

In step 2810, the RSR 120 preferably captures one or more output signals from the accelerometers 305 via the communication interface 145. The output signals captured by the RSR 120 preferably include the output signals of the accelerometers 305. In a preferred embodiment, in step 2810, the RSR 120 further corrects the output signals from the accelerometers 305 for DC offset to produce a corrected output signal. The RSR 120 may correct the output signals using any number of conventional correction methods. In a preferred embodiment, the RSR 120 corrects the output signals by calculating the offset present in each output signal and subtracting that offset from the output signal.

In step 2815, the RSR 120 preferably transforms the corrected output signals from Cartesian coordinates into one or more polar coordinates. The polar coordinates preferably include radius data and angular data.

In step 2820, the RSR 120 preferably analyzes the radius data to find the peak radius and the root-mean-square radius. The RSR 120 may analyze the radius data using any number of conventional analysis methods. In a preferred embodiment, in step 2820, the RSR 120 further sorts the angular data into sorted angular data. The sorted angular data is preferably sorted into one or more 30-degree bins. The RSR 120 may sort the angular data using any number of conventional sorting methods. The radius data preferably specifies the acceleration magnitude. In a preferred embodiment, in step 2820, the RSR 120 further weights the sorted angular data by the magnitude of the radius data. The RSR 120 preferably weights the sorted angular data by finding, for each angular data point, the corresponding radius data point and by calculating a sum of the radius data points within each 30-degree bin. In an alternate embodiment, the RSR 120 weights the sorted angular data by finding, for each angular data point, the corresponding radius data point and by calculating a sum of the square of each radius data point within each 30-degree bin. In a preferred embodiment, in step 2820, the RSR 120 further identifies a direction and a magnitude of a noise signal being produced by the sensor assembly 210. The RSR 120 may identify the direction of the noise signal using the 30-degree bins with the largest weight. The RSR 120 may identify the magnitude of the noise signal using any common magnitude measurement method. In an alternate embodiment, the angular data bins may be less than 30-degrees. In an alternate embodiment, the angular data bins may be more than 30-degrees.

Figure 29:
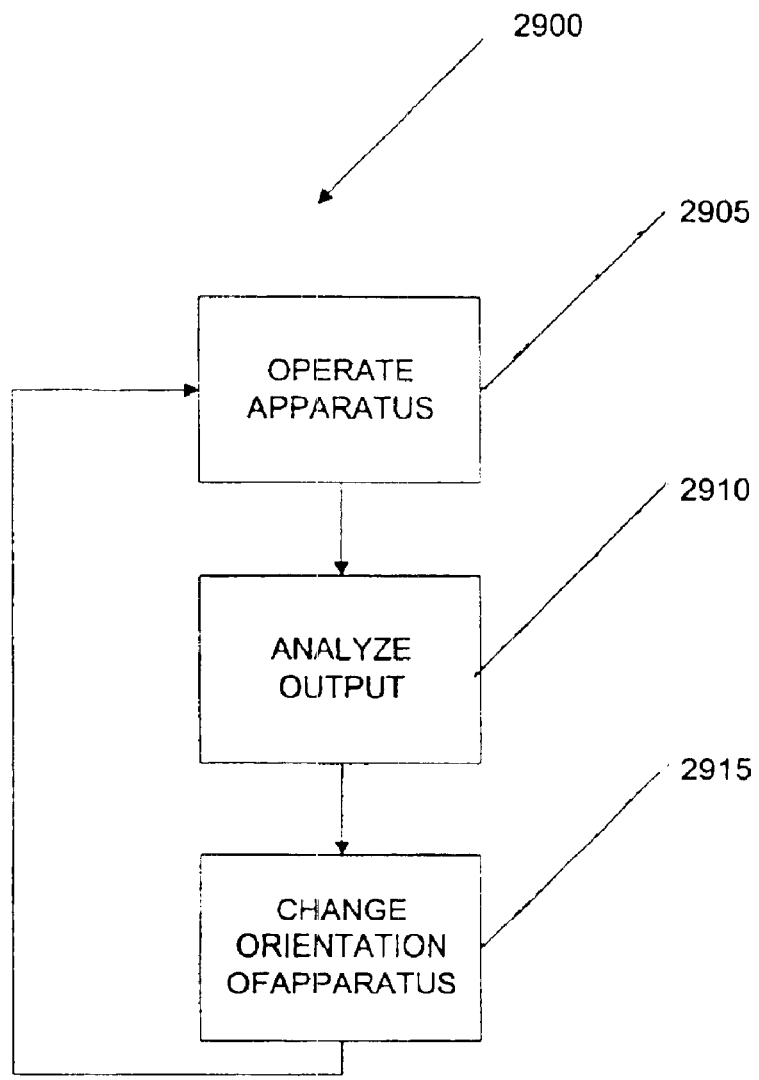
FIG. 29 is a block diagram of an alternate embodiment of a method for determining the state-of-health of the sensor assembly of FIG. 2 of the system of FIG. 1.

Referring to FIG. 29, another embodiment of a method 2900 for determining the state-of-health of the sensor assembly 210 includes: (1) operating the sensor assembly 210 in step 2905; (2) analyzing an output signal in step 2910; (3) and changing the orientation of the sensor assembly 210 in step 2915.

In step 2905, the accelerometers 305 of the sensor assembly 210 are preferably operated. The accelerometers 305 may be operated using any number of conventional operating methods. In a preferred embodiment, the accelerometers 305 are operated such that they produce a measurement of the gravity field in order to provide orientation measurements.

In step 2910, the RSR 120 preferably collects one or more output signals from the accelerometers 305 via the communication interface 145. In a preferred embodiment, the output signals include a self-measured coefficient of gravity for each of the accelerometers 305. The RSR 120 may collect the output signals using any number of conventional collection methods. In a preferred embodiment, the RSR 120 collects the output signals using balanced transmission on a twisted wire pair in order to optimally provide reliable data transfer. In a preferred embodiment, in step 2910, the RSR 120 further analyzes the output signals from the accelerometers 305. The RSR 120 may analyze the output signals using any number of conventional analysis methods. In a preferred embodiment, in step 2910, the RSR 120 further calculates a vector sum of the self-measured coefficients of gravity and uses the vector sum to calculate the angle of each accelerometer 305 with respect to gravity. The RSR 120 may calculate the vector sum and angle using any number of conventional calculation methods. In a preferred embodiment, in step 2910, the RSR 120 further compares the calculated angle of each accelerometer 305 to the known angle of each accelerometer 305. The error may range, for example, from about 0° to 5°. In a preferred embodiment, the error ranges from about 0.01° to 2° in order to optimally provide verification of accelerometer operation.

In step 2915, the orientation of the sensor assembly 210 is preferably changed. The orientation may be changed using any number of conventional rotation methods. In a preferred embodiment, the orientation is changed using a fixture built to hold the sensor module 105 and to provide multiple orientations in order to optimally provide accurate orientation of the sensor module 105.

The method 2900 is preferably repeated to operate all the accelerometers 305 in a plurality of orientations. The plurality of orientations preferably include: horizontal, right-side-up; vertical; horizontal, upside-down; Galperin angle, right-side-up; and Galperin angle, upside down. The Galperin angle is the orientation wherein the 3-axis diagonal of the accelerometers 305 is placed vertical. In a preferred embodiment, all operations of all orientations for all of the accelerometers 305 preferably are within the error range stated in step 2910 to indicate that the sensor assembly 210 is acceptable.

Figure 30:
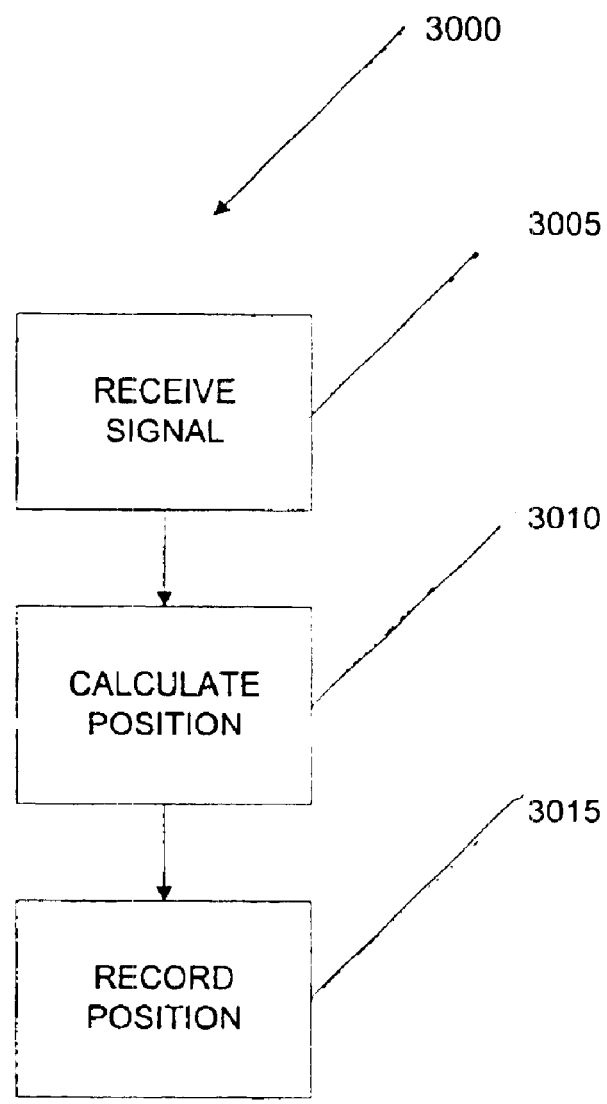
FIG. 30 is a block diagram of an embodiment of a method for determining the position of the sensor module of FIG. 1.

Referring to FIG. 30, a preferred embodiment of a method 3000 for determining the position of the sensor module 105 includes: (1) receiving a signal in step 3005; (2) calculating a position in step 3010; and (3) recording the position in step 3015.

In step 3005, the RSR 120 preferably receives differential correction information from an external source. The RSR 120 may receive the differential correction information via any number of data communication methods. In a preferred embodiment, the RSR 120 receives the differential correction information via radio transmission in order to simplify system 100 deployment. In a preferred embodiment, in step 3005, the RSR 120 further telemeters the differential correction information to the sensor module 105 via the communication interface 145. The RSR 120 may telemeter the differential correction information using any number of conventional transmission methods. In a preferred embodiment, the RSR 120 telemeters the differential correction information using balanced transmission on a twisted wire pair in order to optimally provide reliable data transfer. In a preferred embodiment, in step 3005, the sensor module 105 further transfers the differential correction information to the GPS receiver 230.

In step 3010, the GPS receiver 230 preferably determines the 3-axis position of the sensor module 105 using the transmissions from the GPS satellites visible to the antenna 205 and the differential correction information received in step 3005. The location of the sensor module 105 may be calculated at periodic intervals or on command from the RSR 120.

In step 3015, the GPS receiver 230 preferably transfers the 3-axis position to the controller 220. The sensor module 105 preferably transfers the 3-axis position to the RSR 120 via the communication interface 145. The 3-axis position may be transferred using any number of conventional transfer methods. In a preferred embodiment, the 3-axis position is transferred using balanced transmission on a twisted wire pair in order to optimally provide reliable data transfer. The RSR 120 preferably stores the 3-axis position in the memory 605.

Figure 31:
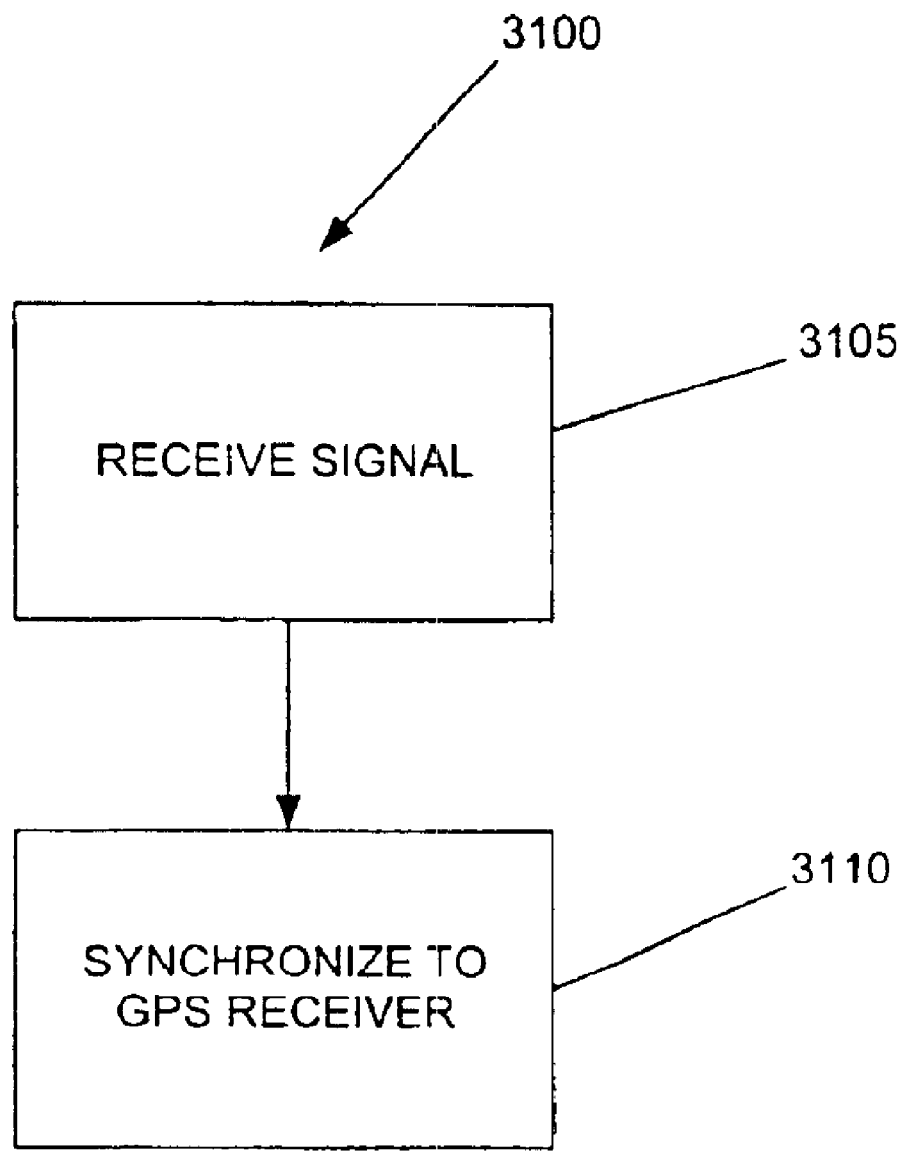
FIG. 31 is a block diagram of an embodiment of a method for synchronizing the operation of the sensor module of FIG. 1.

Referring to FIG. 31, a preferred embodiment of a method 3100 for synchronizing the operation of the sensor module 105 to a common time-base includes: (1) receiving a signal in step 3105; and (2) synchronizing to the GPS receiver 230 in step 3110.

In step 3105, the RSR 120 preferably receives a shot event list from an external source. The RSR 120 may receive the shot event list via any conventional data communication methods. In a preferred embodiment, the RSR 120 receives the shot event list via radio transmission in order to reduce the weight of the system 100 and simplify deployment of the system 100. The shot event list may be, for example, a single or multiple entry planned shot event list. The RSR 120 transfers the shot event list to the sensor module 105 via the communication interface 145. The RSR 120 may transfer the shot event list using any number of conventional transfer methods. In a preferred embodiment, the RSR 120 transfers the shot event list using balanced transmission on a twisted wire pair in order to optimally provide reliable data transfer. In a preferred embodiment, in step 3105, the GPS receiver 230 further provides a signal. The signal may be, for example, a time value produced on demand, 1 pulse per second, or any other synchronization signal provided by the GPS receiver 230. In a preferred embodiment, the signal is 1 pulse per second in order to provide compatibility with most commercially available GPS receivers. The controller 220 of the sensor module 105 preferably includes a clock.

In step 3110, the clock within the controller 220 is preferably synchronized to the signal from the GPS receiver 230 of the sensor module 105. The synchronization may be done using any number of conventional synchronization methods. In a preferred embodiment, the synchronization matches a time counter in the controller 220 with the time produced by the GPS receiver 230 in order to optimally provide accurate data acquisition start times. In an alternate embodiment, the RSR 120 preferably communicates the shot event list to one or more sensor modules 105 for use in synchronizing one or more sensor modules 105.

Figure 32:
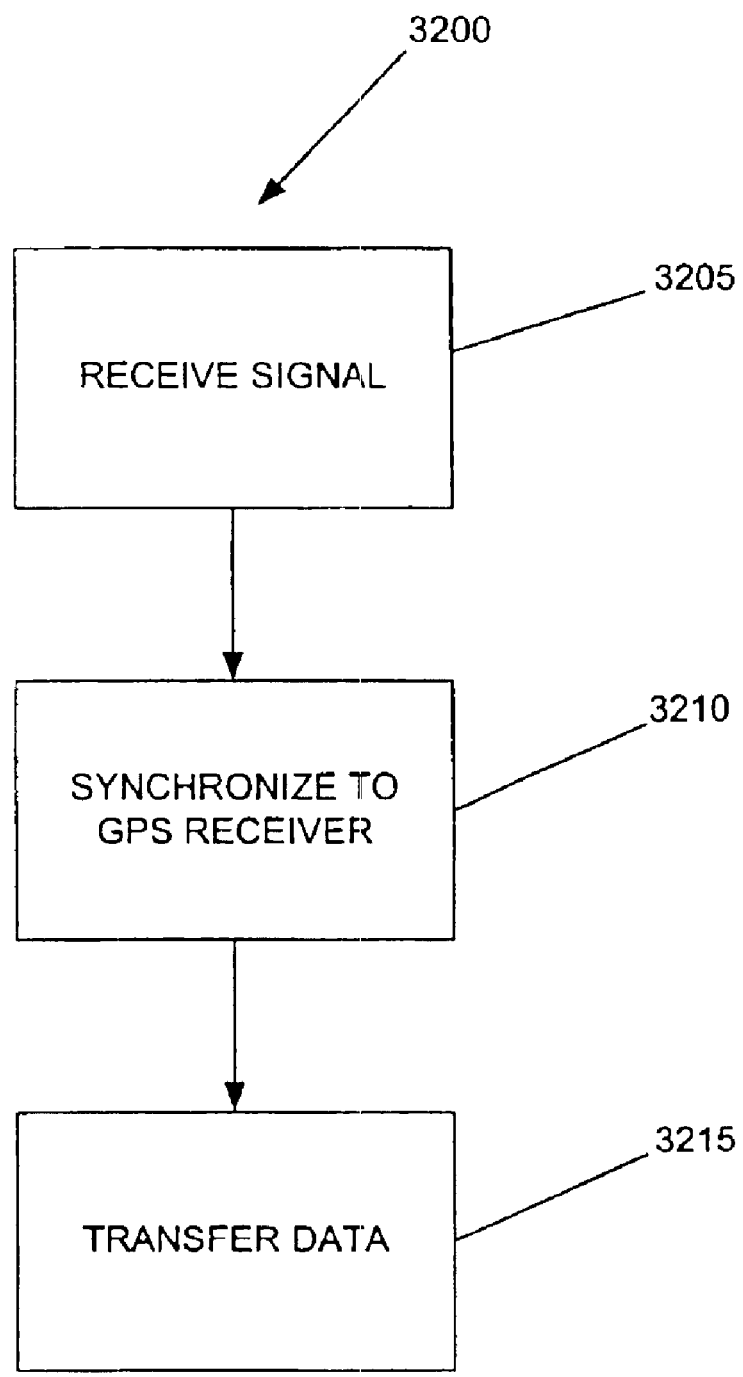
FIG. 32 is a block diagram of an alternate embodiment of a method for synchronizing the operation of the system of FIG. 1.

Referring to FIG. 32, another embodiment of a method 3200 for synchronizing the operation of the sensor module 105 includes: (1) receiving a signal in step 3205; (2) synchronizing to the GPS receiver 615 in step 3210; and (3) transferring data in step 3215.

In step 3205, the RSR 120 preferably receives a shot list from an external source. The RSR 120 may receive the shot event list via any number of conventional communication methods. In a preferred embodiment, the RSR 120 receives the shot event list via radio transmission in order to reduce the weight of the system 100 and to simplify deployment of the system 100. The shot event list may be, for example, a single or multiple entry planned shot event list. In a preferred embodiment, in step 3205, the GPS receiver 615 of the RSR 120 further provides a signal. The signal may be, for example, a time value produced on demand, 1 pulse per second, or any other synchronization signal provided by the GPS receiver 615. In a preferred embodiment, the signal is 1 pulse per second in order to provide compatibility with most commercially available GPS receivers. The controller 610 of the RSR 120 preferably includes a clock.

In step 3210, the clock within the host controller 610 is preferably synchronized to the 1 pulse per second signal provided by the GPS receiver 615. The synchronization may be done using any number of conventional synchronization methods. In a preferred embodiment, the synchronization matches a time counter in the controller 610 with the time produced by the GPS receiver 615 in order to optimally provide accurate data acquisition start times.

In step 3215, the RSR 120 preferably transfers the synchronization signal to the sensor module 105 via the communication interface 145. The RSR 120 may transfer the signal using any number of conventional transfer methods. In a preferred embodiment, the RSR 120 transfers the signal using balanced transmission on a twisted wire pair in order to provide reliable data transfer.

In an alternate embodiment, the RSR 120 preferably transfers the signal to one or more sensor modules 105 via the communication interface 145.

Figure 33:
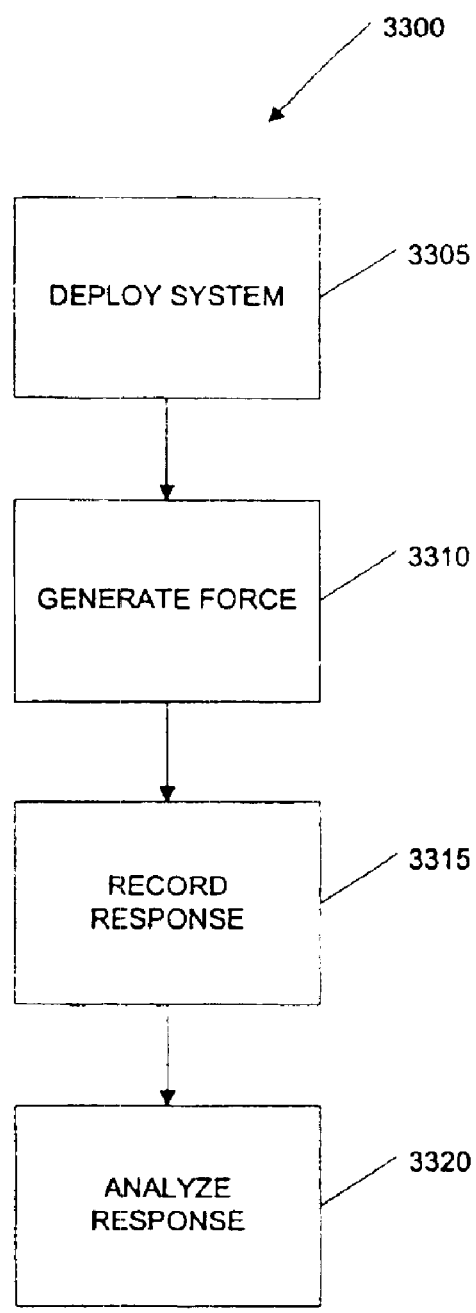
FIG. 33 is a block diagram of an embodiment of a method for determining the vector fidelity of the sensor module in FIG. 1.

Referring to FIG. 33, a preferred embodiment of a method 3300 for determining the vector fidelity of the sensor module includes: (1) deploying the sensor module 105 in step 3305; (2) generating a force in step 3310; (3) recording a response in step 3315; and (4) analyzing the response in step 3320.

In step 3305, the sensor module 105 is preferably deployed beneath the Earth's surface. The sensor module 105 may be deployed using any number of conventional deployment methods. In a preferred embodiment, the sensor module 105 is deployed in a shallow tight fitting hole in order to optimally provide coupling and noise isolation.

In step 3310, the crystal assembly 225 preferably generates a force. In a preferred embodiment, the force is the impulse 710. In an alternate embodiment, the force is the impulses 810. The force may be generated using any number of conventional force generating methods. In a preferred embodiment, the force is generated from the piezocrystals 705. The piezocrystals 705 are preferably charged to a high voltage. The piezocrystals 705 preferably shift from their resting position due to the high voltage. The high voltage of the piezocrystals 705 is preferably discharged. The piezocrystals 705 preferably create the force as the piezocrystals 705 return to their resting position.

In step 3315, the forces created in step 3310 preferably create a response in the sensor module 105. The response of the sensor module 105 is preferably an output signal. The output signal from the sensor module 105 may be transferred to any number of conventional analysis or recording apparatus. The sensor module 105 output signal is preferably transferred to the RSR 120 via the communication interface 145. The output signal from the sensor module 105 may be transferred to the RSR 120 using any number of conventional transfer methods. In a preferred embodiment, the output signal from the sensor module 105 is transferred to the RSR 120 using balanced transmission on a twisted wire pair in order to optimally provide reliable data transfer. The RSR 120 preferably collects the output signal of the sensor module 105 for analysis.

In step 3320, the RSR 120 preferably analyzes the output signal from the sensor module 105. The RSR 120 may analyze the output signal using any number of conventional analysis methods. The RSR 120 preferably analyzes the output signal by comparing the magnitudes of the output signals corresponding to the different axes of sensitivity 310 of the sensor module 105. In a preferred embodiment, in step 3320, the RSR 120 further calculates a vector fidelity of the sensor module 105. The RSR 120 may calculate the vector fidelity of the sensor module 105 using any number of conventional calculation methods. In a preferred embodiment, the RSR 120 calculates the vector fidelity of the sensor module 105 using the difference in the amplitudes of the output signals corresponding to the different axes of sensitivity 310 in order to optimally provide a measure of the vector fidelity of the sensor module 105.

Although illustrative embodiments of the invention have been shown and described, a wide range of modification, changes and substitution is contemplated in the foregoing disclosure. In some instances, some features of the present invention may be employed without a corresponding use of the other features. Accordingly, it is appropriate that the appended claims be construed broadly and in a manner consistent with the scope of the invention.

What is claimed is:

1. A method of acquiring seismic data comprising:

sensing seismic energy with one or more sensor modules, wherein the one or more sensor modules comprise one or more force feedback controlled accelerometers;

recording seismic data indicative of the seismic energy using a seismic recorder; and determining a state-of-health for the sensor module comprising:

operating the accelerometer for a period of time; and analyzing an output signal generated by the accelerometer;

wherein analyzing an output signal comprises detecting an excessive root-mean-square amplitude response of the output signal to indicate a malfunction of the accelerometer or a noisy environment.

2. A method of acquiring seismic data comprising:

sensing seismic energy with one or more sensor modules, wherein the one or more sensor modules comprise three or more accelerometers;

recording seismic data indicative of the seismic energy using a seismic recorder; and determining a state-of-health for the sensor module comprising:

operating the accelerometers;

driving two of the accelerometers at a reference frequency;

monitoring an output signal generated by an undriven accelerometer; and rotating through all the accelerometers;

wherein monitoring an output signal comprises monitoring the magnitude of the reference frequency in the output signal of the undriven accelerometer to detect a malfunction of the sensor module.

3. A method of acquiring seismic data comprising:

sensing seismic energy with one or more sensor modules, wherein the one or more sensor modules comprise one or more accelerometers;

recording seismic data indicative of the seismic energy using a seismic recorder; and determining a state-of-health for the sensor module comprising:

operating the accelerometers for a period of time;

removing a DC offset from one or more output signals generated by the accelerometer to produce one or more resulting signals;

transforming the resulting signals from the accelerometers from Cartesian coordinates into polar coordinates; and analyzing the polar coordinates;

wherein analyzing the polar coordinates comprises analyzing one or more peak and root-mean-square amplitude results to indicate a malfunction of the sensor module or a noisy acquisition environment.

* * * * *